(12) United States Patent
Fauq et al.

(10) Patent No.: US 8,563,760 B2
(45) Date of Patent: Oct. 22, 2013

(54) PROCESS FOR THE SYNTHESIS OF LONG-CHAIN FATTY ACIDS

(75) Inventors: Abdul H. Fauq, Jacksonville, FL (US); Albert O. Edwards, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 345 days.

(21) Appl. No.: 12/871,043

(22) Filed: Aug. 30, 2010

(65) Prior Publication Data

US 2011/0105781 A1    May 5, 2011

Related U.S. Application Data

(60) Provisional application No. 61/238,509, filed on Aug. 31, 2009.

(51) Int. Cl.
- C07C 53/126 (2006.01)
- C07C 57/03 (2006.01)

(52) U.S. Cl.
USPC .......................................... 554/85; 562/598

(58) Field of Classification Search
None
See application file for complete search history.

(56) References Cited

U.S. PATENT DOCUMENTS

| | | | |
|---|---|---|---|
| 4,548,990 A | 10/1985 | Mueller et al. | |
| 2004/0009222 A1 | 1/2004 | Chou et al. | |

OTHER PUBLICATIONS

Ballini. Tetrahedron, 1997, 53 (21), 7341-46.*
Agbada et al., "Role of Stargardt-3 macular dystrophy protein (ELOVL4) in the biosynthesis of very long chain fatty acids," *Proceedings of the National Academy of Sciences*, 2008, 105(35):12843-12848.
Bäckvall, Jan E., et al., "Synthesis of (5E,9E)-5,9-hexacosadienoic acid via copper- and palladium-mediated reactions using 1-acetoxy-4-chloro-2-butene as a synthon", *Acta Chemica Scandinavica, Series B: Organic Chemistry and Biochemistry*, (1988), B42(6), 397-402.
Ballini et al., "C-C bond fission via sulphones: A new cleavage of cyclic β-keto phenylsulphones," *Tetrahedron*, 1997, 53(21): 7341-46.
Capdevila, et al., "A Convergent and Highly Efficient Synthesis of (E,Z)-2,13-Octadecadienyl Acetate and (E,Z)-3,13-Octadecadienyl Acetate, Components of the Sex Pheromone of the Leopard Moth *Zeuzera pyrina*, through Sulfones", *Organic Letters* (1999), 1(6), 845-848.
Cheskis, B. A., et al., "Stereospecific synthesis of transoid mono- and 1,3-dienic pheromones of Lepidoptera from secondary cyclopropylcarbinols", *Izvestiya Akademii Nauk SSSR, Seriya Khimicheskaya*, (1990), (11), 2539-44 (with English abstract).
Edwards and Malek, "Molecular genetics of AMD and current animal models," Angiogenesis, 2007, 10(2):119-32, Epub Mar. 13, 2007.
Einmahl, "Therapeutic applications of viscous and injectable poly(ortho) esters," *Adv. Drug Deliv. Rev.*, 2001, 53:45-73.
Fabrizio and Salminem "Ocular inserts for topical delivery," *Adv. Drug Deliv. Rev.*, 1998, 16:95-106.
Ghelardi et al., "In Vivo Imaging of Bioluminescent *Escherichia coli* in a Cutaneous Wound Infection Model for Evaluation of an Antibiotic Therapy," *Antimicrob. Agents Chemother.*, 2004, 48:3396-3401.
Berge et al., "Pharmaceutical Salts", *J. of Pharmaceutical Science*, 1977, 66(1) pp. 1-19.
Julia, et al., Syntheses via sulfones. XXXVII. Synthesis of three pheromones with a Z double bond: (Z)-8-DDA, (Z)-9-DDA, and (Z)-9-TDA, *Tetrahedron* (1986), 42(9), 2469-74 (English Abstract).
McMahon et al., "Retinal pathology and skin barrier defect in mice carrying Stargardt-3 disease-3 mutation in elongase of very long chain fatty acids-4," *Molecular Vision*, 2007, 13:258-272.
Miyakoshi, et al., "Synthesis of (±)-lauthisan," *Heterocycles* (2007), 74, 185-189.
Ravin, Louis J., "Preformulation", *Remington's Pharmaceutical Sciences*, 17th ed., Chapter 76, Mack Publishing Company, Easton, Pa., 1985, p. 1409-1423.
Wagh et al., "Polymers used in ocular dosage form and drug delivery systems," *Asian J. Pharm.*, Jan. 2008, 2(1):12-17.

* cited by examiner

*Primary Examiner* — Noble Jarrell
(74) *Attorney, Agent, or Firm* — Fish & Richardson P.C.

(57) ABSTRACT

This invention relates to processes for preparing long-chain fatty acids of Formula I:

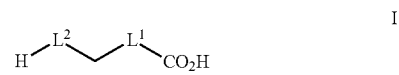

and salts thereof, as well as intermediates for the processes, wherein $L^1$ and $L^2$ are described herein.

31 Claims, No Drawings

PROCESS FOR THE SYNTHESIS OF LONG-CHAIN FATTY ACIDS

This application claims the benefit of priority of U.S. Prov. Appl. No. 61/238,509, filed Aug. 31, 2009, which is incorporated herein by reference in its entirety.

STATEMENT AS TO FEDERALLY SPONSORED RESEARCH

This invention was made with government support under EY014467 awarded by the National Institutes of Health. The government has certain rights in the invention.

TECHNICAL FIELD

This invention relates to processes for preparing long-chain fatty acids, as well as intermediates for the processes.

BACKGROUND

Long-chain fatty acids are essential for normal function of cell membranes and as precursors for neuroprotective and inflammatory molecules. For example, very long chain polyunsaturated fatty acids (VLPUFAs) are present in the human retina and play an important role in maintaining the structure and function of the retina. A disease with a defect in the gene that synthesizes VLPUFAs in the retina leads to an early onset degeneration of the macula and severe loss of vision. Many VLPUFAs and other very long chain fatty acids are not commercially available. Accordingly, there is a need to develop new methods for preparing long-chain fatty acids, including VLPUFAs. This application addresses this need and others.

SUMMARY

The present invention provides, inter alia, processes of preparing a compound of Formula I:

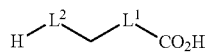

I or salt thereof; comprising desulfonating a compound of Formula II:

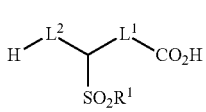

II to form a compound of Formula I; wherein:
  $L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
  $L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;
  $R^1$ is phenyl, which is optionally substituted by 1, 2, 3, 4, or 5 independently selected $R^{1a}$ groups;
  each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$alkylcarbamyl, di($C_{1-6}$)alkylcarbamyl, $C_{1-6}$alkoxycarbonyl, and $C_{1-6}$alkylsulfonyl; and
  each $R^a$ and $R^b$ is independently selected from $C_{1-30}$ alkyl and $C_{2-30}$ alkenyl.

The present invention also provides processes of preparing a compound of Formula I:

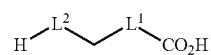

I or salt thereof; comprising:
(a) protecting a compound of Formula IX:

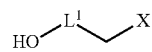

IX to form a compound of Formula VIII:

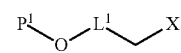

VIII (b) reacting a compound of Formula VIII with a compound of formula $R^1SH$ in the presence of sodium methoxide to form a compound of Formula VII:

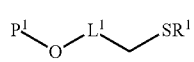

VII (c) oxidizing the compound of Formula VII to form a compound of Formula V:

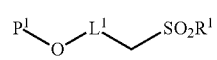

V (d) treating the compound of Formula V with n-butyllithium, followed by reacting with a compound of Formula VI:

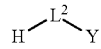

VI to form a compound of Formula IV:

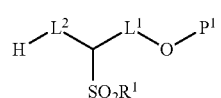

IV (e) deprotecting the compound of Formula IV to form a compound of Formula III:

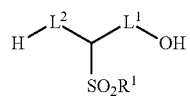

(f) oxidizing the compound of Formula III to form a compound of Formula II:

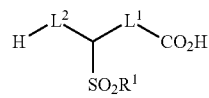

and (g) desulfonating the compound of Formula II to form the compound of Formula I or salt thereof;

wherein:

$P^1$ is tert-butyldimethylsilyl;

Y is p-toluene sulfonyloxy;

X is halogen;

$L^1$ is selected from $C_{8-50}$ straight-chain alkylene and $C_{4-50}$ straight-chain alkenylene;

$L^2$ is selected from $C_{10-50}$ straight-chain alkylene and $C_{4-50}$ straight-chain alkenylene; and $R^1$ is phenyl.

The present invention also provides intermediate compounds of Formula II:

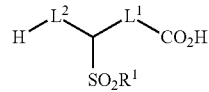

or salts thereof; wherein:

$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$alkyl, $C_{1-6}$haloalkyl, $C_{1-6}$alkoxy, $C_{1-6}$haloalkoxy, di($C_{1-6}$alkyl)amino, carbamyl, $C_{1-6}$alkylcarbamyl, di($C_{1-6}$)alkylcarbamyl, $C_{1-6}$alkoxycarbonyl, and $C_{1-6}$ alkylsulfonyl; and each $R^a$ and $R^b$ is independently selected from $C_{1-30}$ alkyl and $C_{2-30}$ alkenyl.

The present invention further provides intermediate compounds of Formula V:

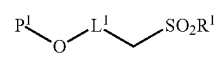

or salts thereof; wherein:

$P^1$ is a hydroxyl protecting group;

$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$alkyl, $C_{1-6}$haloalkyl, $C_{1-6}$alkoxy, $C_{1-6}$haloalkoxy, di($C_{1-6}$alkyl)amino, carbamyl, $C_{1-6}$alkylcarbamyl, di($C_{1-6}$)alkylcarbamyl, $C_{1-6}$alkoxycarbonyl, and $C_{1-6}$alkylsulfonyl; and each $R^a$ is independently selected from $C_{1-30}$ alkyl and $C_{2-30}$ alkenyl.

The present invention further provides processes of preparing a compound of Formula I:

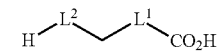

or salt thereof, comprising:

(a) reducing a compound of Formula XVI:

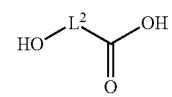

to form a compound of Formula XV:

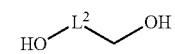

(b) converting a compound of Formula XV:

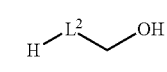

to a compound of Formula XIV:

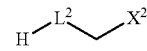

(c) reacting a compound of Formula XIV:

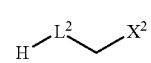

with an anion of formula $R^1SO_2M$ to form a compound of Formula XIII:

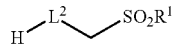

XIII (d) treating the compound of Formula XIII with a strong base, followed by reacting with a compound of Formula XII:

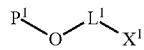

XII to form a compound of Formula IV:

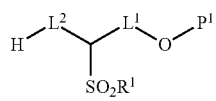

IV (e) desulfonating the compound of Formula IV to form a compound of Formula XVIa:

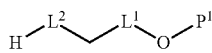

XVIa (f) deprotecting the compound of Formula XVIa:

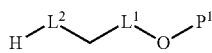

XVIa to form a compound of Formula XVII:

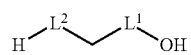

XVII and
(g) oxidizing the compound of Formula XVII:

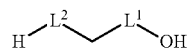

XVII to form the compound of Formula I, or salt thereof;
$P^1$ is a hydroxyl protecting group;
$X^2$ and $X^1$ are each, independently, a leaving group;
$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;
$R^1$ is phenyl, which is optionally substituted by 1, 2, 3, 4, or 5 independently selected $R^{1a}$ groups;
each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and each $R^a$ and $R^b$ is independently selected from $C_{1-30}$ alkyl and $C_{2-30}$ alkenyl.

The present invention further provides processes of preparing a compound of Formula XXI:

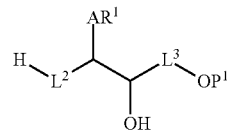

XXI comprising treating a compound of Formula XVIII:

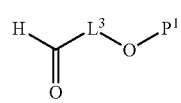

XVIII with a strong base, followed by reacting with a compound of Formula XXII:

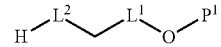

XXII to form a compound of Formula XXI;
wherein:
A is —S— or —S(O)$_2$—;
$P^1$ is a hydroxyl protecting group;
$L^1$ is —CH$_2$-L$^3$-;
$L^3$ is selected from $C_{3-50}$ straight-chain alkylene and $C_{3-50}$ straight-chain alkenylene; each of which is optionally substituted with 1, 2, 3, 4, 5, or 6 independently selected $R^a$ groups;
$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;
$R^1$ is phenyl, which is optionally substituted by 1, 2, 3, 4, or 5 independently selected $R^{1a}$ groups;
each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and each $R^a$ and $R^b$ is independently selected from $C_{1-30}$ alkyl and $C_{2-30}$ alkenyl.

The present invention also provides processes of preparing a compound of Formula XVIa:

XVIa comprising reacting a compound of Formula XXVI:

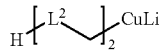
XXVI with a compound of Formula XII:

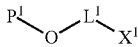
XII to form a compound XVIa; wherein:

X$^1$ is a leaving group;

P$^1$ is a hydroxyl protecting group;

L$^1$ is selected from C$_{4-50}$ straight-chain alkylene and C$_{4-50}$ straight-chain alkenylene; each of which is optionally substituted with 1, 2, 3, 4, 5, or 6 independently selected R$^a$ groups;

L$^2$ is -L$^4$-CH$_2$—;

L$^4$ is selected from C$_{3-50}$ straight-chain alkylene and C$_{3-50}$ straight-chain alkenylene; each of which is optionally substituted with 1, 2, 3, 4, 5, or 6 independently selected R$^b$ groups; and each R$^a$ and R$^b$ is independently selected from C$_{1-30}$ alkyl and C$_{2-30}$ alkenyl.

The present invention further provides processes of preparing a compound of Formula I:

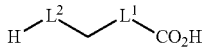
I comprising reducing a compound of Formula XXVII:

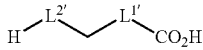
XXVII wherein:

L$^1$ is selected from C$_{4-60}$ straight-chain alkylene and C$_{4-60}$ straight-chain alkenylene; which is optionally substituted with 1, 2, 3, 4, 5, or 6 independently selected R$^a$ groups;

L$^2$ is selected from C$_{4-60}$ straight-chain alkylene and C$_{4-60}$ straight-chain alkenylene; which is optionally substituted with 1, 2, 3, 4, 5, or 6 independently selected R$^b$ groups;

L$^{1'}$ is C$_{4-60}$ straight-chain alkynylene; which is optionally substituted with 1, 2, 3, 4, 5, or 6 independently selected R$^c$ groups;

L$^{2'}$ is C$_{4-60}$ straight-chain alkynylene; which is optionally substituted with 1, 2, 3, 4, 5, or 6 independently selected R$^d$ groups;

each R$^a$ and R$^b$ is independently selected from C$_{1-30}$ alkyl and C$_{2-30}$ alkenyl; and each R$^c$ and R$^d$ is independently selected from C$_{1-30}$ alkyl, C$_{2-30}$ alkenyl, and C$_{2-30}$ alkynyl.

In some embodiments, the compound of Formula XXVII is a compound of Formula Ia:

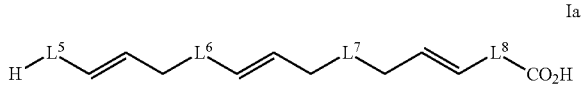
Ia and the compound of Formula XXVII is a compound of Formula XXVIIa:

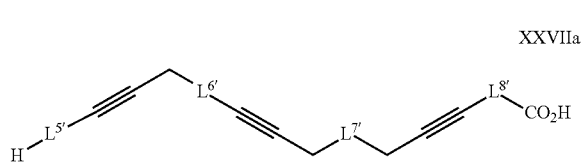
XXVIIa wherein:

L$^5$, L$^6$, L$^7$, and L$^8$ are each independently selected from C$_{2-25}$ straight-chain alkylene and C$_{2-25}$ straight-chain alkenylene; and L$^{5'}$, L$^{6'}$, L$^{7'}$, and L$^{8'}$ are each independently selected from C$_{2-25}$ straight-chain alkylene, C$_{2-25}$ straight-chain alkenylene, and C$_{2-25}$ straight-chain alkynylene.

DETAILED DESCRIPTION

At various places in the present specification, substituents of compounds are disclosed in groups or in ranges. It is specifically intended that the compounds include each and every individual subcombination of the members of such groups and ranges. For example, the term "C$_{1-6}$ alkyl" is specifically intended to individually disclose methyl, ethyl, C$_3$ alkyl, C$_4$ alkyl, C$_5$ alkyl, and C$_6$ alkyl.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

For compounds in which a variable appears more than once, each variable can be a different moiety independently selected from the group defining the variable. For example, where a structure is described having two R groups that are simultaneously present on the same compound, the two R groups can represent different moieties independently selected from the group defined for R.

The compounds described herein can be asymmetric (e.g., having one or more stereocenters). All stereoisomers, such as enantiomers and diastereomers, are intended unless otherwise indicated. Compounds described herein that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds described herein may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid or chiral base which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein, or pharmaceutically acceptable salts thereof, further include hydrates and solvates, as well as anhydrous and non-solvated forms. Compounds described herein can also include all isotopes of atoms occurring in the intermediates or final compounds. Isotopes include those atoms having the same atomic number but different mass numbers. For example, isotopes of hydrogen include tritium and deuterium.

The term, "compound" as used herein is meant to include all stereoisomers, tautomers, and isotopes of the structures depicted.

As used herein, the phrase "optionally substituted" means unsubstituted or substituted. As used herein, the term "substituted" means that a hydrogen atom is removed and replaced by a substitutent. It is understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 12, 1 to 8, 1 to 6, or 1 to 4 carbon atoms. Examples of alkyl moieties include, but are not limited to, chemical groups such as methyl, ethyl, n-propyl, isopropyl, n-butyl, tert-butyl, isobutyl, sec-butyl, 2-methyl-1-butyl, n-pentyl, 3-pentyl, n-hexyl, 1,2,2-trimethylpropyl, n-heptyl, n-octyl, and the like.

As used herein, "alkenyl", employed alone or in combination with other terms, refers to an alkyl group having one or more double carbon-carbon bonds. In some embodiments, the alkenyl moiety contains 2 to 10 or 2 to 6 carbon atoms. Example alkenyl groups include, but are not limited to, ethenyl, n-propenyl, isopropenyl, n-butenyl, sec-butenyl, and the like.

As used herein, "alkynyl", employed alone or in combination with other terms, refers to an alkyl group having one or more triple carbon-carbon bonds, which may also optionally have one or more double carbon-carbon bonds. In some embodiments, the alkynyl moiety contains 2 to 10 or 2 to 6 carbon atoms.

As used herein, "straight chain $C_{n-m}$ alkylene" refers to a non-branched alkyl chain of n to m carbon atoms. In some embodiments, the alkylene chain has 4 to 50, 8 to 50, 10 to 50, 12 to 50, or 20 to 50 carbon atoms.

As used herein, "straight chain $C_{n-m}$ alkenylene" refers to a non-branched alkenyl chain of n to m carbon atoms. In some embodiments, the alkenylene chain has 4 to 50, 8 to 50, 10 to 50, 12 to 50, or 20 to 50 carbon atoms.

As used herein, "straight chain $C_{n-m}$ alkynylene" refers to a non-branched alkynyl chain of n to m carbon atoms. In some embodiments, the alkynylene chain has 4 to 50, 8 to 50, 10 to 50, 12 to 50, 2 to 25, 10 to 25, or 20 to 50 carbon atoms.

As used herein, the term "$C_{n-m}$ alkoxycarbonyl", employed alone or in combination with other terms, refers to a group of formula —C(=O)O-alkyl, wherein the alkyl group has n to m carbon atoms. In some embodiments, the alkyl group has 1 to 6 or 1 to 4 carbon atoms.

As used herein, the term "di($C_{n-m}$-alkyl)amino", employed alone or in combination with other terms, refers to a group of formula —N(alkyl)$_2$, wherein each alkyl groups each has independently n to m carbon atoms. In some embodiments, each alkyl group independently has 1 to 6 or 1 to 4 carbon atoms.

As used herein, the term "carbamyl", employed alone or in combination with other terms, refers to a group of formula —C(=O)NH$_2$.

As used herein, the term "$C_{n-m}$ alkylcarbamyl", employed alone or in combination with other terms, refers to a group of formula —C(=O)—NH(alkyl), wherein the alkyl group has n to m carbon atoms. In some embodiments, the alkyl group has 1 to 6 or 1 to 4 carbon atoms.

As used herein, the term "di($C_{n-m}$-alkyl)carbamyl", employed alone or in combination with other terms, refers to a group of formula —C(=O)—N(alkyl)$_{2i}$ wherein each alkyl group independently has n to m carbon atoms. In some embodiments, each alkyl group independently has 1 to 6 or 1 to 4 carbon atoms.

As used herein, the term "$C_{n-m}$-alkylsulfonyl", employed alone or in combination with other terms, refers to a group of formula —S(=O)$_2$-alkyl, wherein the alkyl has n to m carbon atoms. In some embodiments, the alkyl group has 1 to 6 or 1 to 4 carbon atoms.

As used herein, the term "carbonyl", employed alone or in combination with other terms, refers to a —C(=O)— group.

As used herein, the term "cyano", employed alone or in combination with other terms, refers to a group of formula —CN.

As used herein, the terms "halo" and "halogen", employed alone or in combination with other terms, refer to fluoro, chloro, bromo, and iodo. In some embodiments, halogen is fluoro.

As used herein, the term "$C_{n-m}$ haloalkyl", employed alone or in combination with other terms, refers to an alkyl group having from n to m carbon atoms and one halogen atom to 2x+1 halogen atoms which may be the same or different, where "x" is the number of carbon atoms in the alkyl group. In some embodiments, the halogen atoms are fluoro atoms. In some embodiments, the alkyl group has 1 to 6 or 1 to 4 carbon atoms. An example of a haloalkyl group is —CF$_3$.

As used herein, "$C_{n-m}$ haloalkoxy", employed alone or in combination with other terms, refers to a group of formula —O-haloalkyl, wherein the haloalkyl group has n to m carbon atoms. In some embodiments, the alkyl group has 1 to 6 or 1 to 4 carbon atoms. An example haloalkoxy group is —OCF$_3$.

As used herein, the term "$C_{n-m}$ fluorinated alkyl", employed alone or in combination with other terms, refers to a $C_{n-m}$ haloalkyl wherein the halogen atoms are selected from fluorine. In some embodiments, fluorinated $C_{n-m}$ haloalkyl is fluoromethyl, difluoromethyl, or trifluoromethyl.

As used herein, the phrase "hydroxyl protecting group" refers to a protecting groups for a hydroxyl group. Appropriate hydroxyl protecting groups are delineated in Wuts and Greene, Protective Groups in Organic Synthesis, 4th ed., John Wiley & Sons: New Jersey (2007), which is incorporated herein by reference in its entirety (in particular, those at pages 16-366) and as described supra.

Unless otherwise indicated herein, the point of attachment of a substituent is generally in the last portion of the name (e.g., arylalkyl is attached through the alkylene portion of the group).

Unless indicated otherwise, the term "about" means plus or minus 10% of the value.

As used herein, the expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The starting materials for the processes described herein are either known in the art or may be synthesized by known synthetic routes. The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, or spectrophotometry (e.g., UV-visible); or by chromatography such as high performance liquid chromatography (HPLC) or thin layer chromatography (TLC).

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The compounds can also include salt forms of the compounds and intermediates described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents.

The compounds and intermediates also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3- dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds, intermediates, and salts thereof, can be substantially isolated. By "substantially isolated" is meant that the compound is at least partially or substantially separated from the environment in which it was formed or detected. Partial separation can include, for example, a composition enriched in the compound or intermediate, or salt thereof. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds, intermediates, and their salts are routine in the art.

In some embodiments, the present invention provides a compound of Formula II:

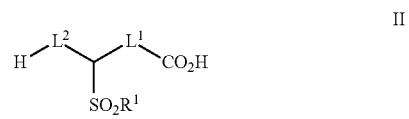

or salt thereof; wherein:

$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$ haloalkyl, $C_{1-6}$ alkoxy, $C_{1-6}$haloalkoxy, di($C_{1-6}$ alkyl)amino, $C_{1-6}$ carbamyl, $C_{1-6}$ alkylcarbamyl, di($C_{1-6}$)alkylcarbamyl, $C_{1-6}$ alkoxycarbonyl, and $C_{1-6}$ alkylsulfonyl; and each $R^a$ and $R^b$ is independently selected from $C_{1-30}$ alkyl and $C_{2-30}$ alkenyl.

In some embodiments, the compound of Formula I can be prepared by the following process (see e.g., Scheme 1, wherein, in some embodiments, the process may be used to produce an isotopically labeled product).

Scheme 1

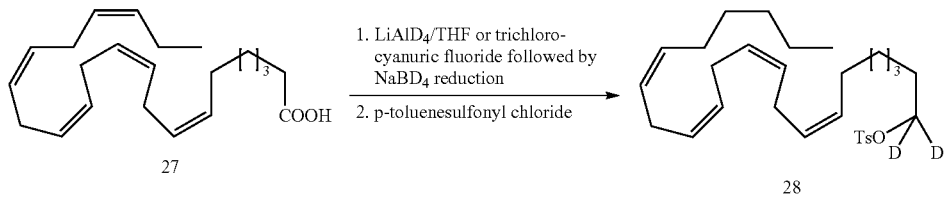

tert-butyldiphenyl(12-(phenylsulfonyl)dodecyloxy)silane

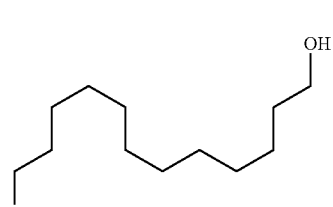

12-bromododecan-1-ol
(n = 1)
Or
14-bromodoadecan-1-ol (n = 3)

1. t-butyldimethylsilyl chloride imidazole, THF
2. C₆H₅SH, CH₃ONa/MeOH
3. m-chlorobperoxy-benzoic acid

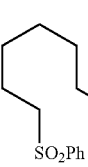

29 n-butyllithium/THF,
−78 to r.t

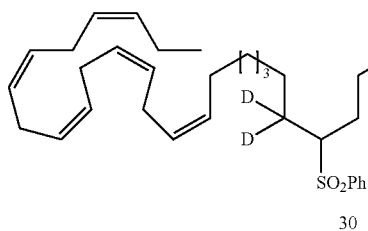

30

1. $(C_4H_9)_4NF/THF$
2. Jone's oxidation
3. 5% Na/Hg/MeOH

31

C34:5 (n-3)·d₂

Accordingly, in some embodiments, the present invention provides a process of preparing a compound of Formula I:

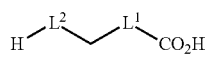

I or salt thereof; comprising desulfonating a compound of Formula II:

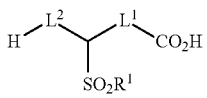

II or salt thereof, to form a compound of Formula I; wherein:

$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$ alkoxy, $C_{1-6}$ haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$ alkylsulfonyl; and each $R^a$ and $R^b$ is independently selected from $C_{1-30}$ alkyl and $C_{2-30}$ alkenyl.

In some embodiments, the desulfonating comprises treating with (1) sodium-mercury amalgam; (2) about 5 to about 15% Na/Hg in methanol or buffered MeOH containing phosphate salts; (3) Mg in methanol; (4) Mg in methanol and HgCl₂; (5) Raney Ni; (6) lithium aluminum hydride; (7) Al—Hg; (8) Mg in ethanol in the presence of dimethoxyethane, triphenylphosphine, and lithium aluminum hydride; (8) NaH and Ni(OAc)₂ in an alcohol; (9) lithium aluminum hydride, NiBr₂, dimethoxyethane, and triphenylphosphine; or (10) Al—Hg in water/tetrahydrofuran.

In some embodiments, the compound of Formula I is (17Z, 20Z,23Z,26Z)-dotriaconta-17,20,23,26-tetraenoic acid, or salt thereof.

In some embodiments, the compound of Formula II:

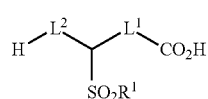

II or salt thereof, is prepared by a process comprising oxidizing a compound of Formula III:

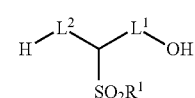

III or salt thereof, to form the compound of Formula II; wherein:

$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$ haloalkyl, $C_{1-6}$ alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$ alkoxycarbonyl, and $C_{1-6}$alkylsulfonyl; and each $R^a$ and $R^b$ is independently selected from $C_{1-30}$ alkyl and $C_{2-30}$ alkenyl.

In some embodiments, the oxidizing includes use of any oxidizing agent useful for converting a primary alcohol to a carboxylic acid, including but not limited to those in Chapter 19 of March, "Advanced Organic Chemistry", which is hereby incorporated by reference in its entirety. In some embodiments, the oxidizing comprises Jones' oxidation (e.g, treating with chromium trioxide and sulfuric acid), either homogeneous phase or two-phase Jones' oxidation, or first partially oxidizing an alcohol to an aldehyde by swern oxidation, or by pyridinium chlorochromate oxidation or pyridinium dichromate oxidation, then further oxidizing the aldehydet to carboxylic acid by using, for example, silver oxide, or oxygen or any other means. In some embodiments, the direct oxidizing comprises (1) Jones' oxidation; (2) oxygen in the presence of catalytic amounts of N-hydroxyphthalamide with or without Co(acac)$_3$; (3) oxygen in presence of catalytic RuCl$_3$—Co(OAc)$_2$ and acetaldehyde; (4) H$_2$O$_2$; (5) H$_2$O$_2$ with cat. [(C$_8$H$_{17}$)$_3$PO$_4$[W(O)(O$_2$)$_2$]$_4$; (6) H$_2$O$_2$ with cat. RuCl$_3$.3H$_2$O; (7) nickel peroxide with NaOH; (8) acetic acid with catalytic Ru—C; (9) nitric acid and CrO$_3$/AcOH; (10) K$_2$Cr$_2$O$_7$ in sulfuric acid; (11) pyridinium dichromate in DMF; (12) K$_2$SO$_5$ with K$_2$Ru$_2$O$_4$; (13) RuCl$_3$ with K$_2$S$_2$O$_8$ and KOH; (14) AgO; (15) NaOCl with cat. TEMPO, NaHCO$_3$, KBr in the presence or absence of Aliquot 336; (16) NaBrO$_2$.3H$_2$O, cat 4-PhCO$_2$-TEMPO, and NaHCO$_3$; (17) NaIO4, cat. RuCl$_3$, H$_2$O, CH$_3$CN, CCl$_4$; (18) NaIO$_4$, cat. RuO$_2$, H$_2$O; (19) H$_5$IO$_6$, cat. RuCl$_3$.H$_2$O, H$_2$O, CH$_3$CN, CCl$_4$; (19) any of microbial oxidation method known in the art, such as *Pseudomonas aeruginosa*.

In some embodiments, the compound of Formula III:

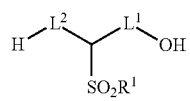

III or salt thereof, is prepared by a process comprising deprotecting a compound of Formula IV:

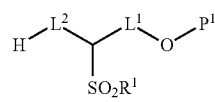

IV to form the compound of Formula III; wherein:
$P^1$ is a hydroxyl protecting group;
$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;
$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$ alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$ alkoxycarbonyl, and $C_{1-6}$alkylsulfonyl; and each $R^a$ and $R^b$ is independently selected from $C_{1-30}$ alkyl and $C_{2-30}$ alkenyl.

Appropriate $P^1$ protecting groups include, but are not limited to the protecting groups for hydroxyl groups delineated in Wuts and Greene, Protective Groups in Organic Synthesis, 4th ed., John Wiley & Sons: New Jersey (2007), which is incorporated herein by reference in its entirety (in particular, those at pages 16-366). In some embodiments, $P^1$ is a silyl ether. In some embodiments, $P^1$ is trimethylsilyl, triisopropylsilyl, dimethylisopropylsilyl, diethylisopropylsilyl, dimethylthexylsilyl, 2-norbornyldimethylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, bis-(tert-butyl)-1-pyrenylmethoxysilyl, tris(trimethylsilyl)silyl(sisyl), (2-hydroxystyryl)dimethylsilyl, (2-hydroxystyryl)diisopropylsilyl, tert-butylmethoxyphenylsilyl, tert-butoxydiphenylsilyl, 1,1,3,3-tetraisopropyl-3-[2-(triphenylmethoxy)ethoxy)disiloxane-1-yl) or fluorous silyl. $P^1$ is tert-butyldimethylsilyl. In some embodiments, $P^1$ is tert-butyldiphenylsilyl. In some embodiments, the protecting group is trimethylsiylethoxymethyl, 2-trimethylsilyethyl, p-methoxybenzyl, 3,4-dimethoxybenzyl, 2,2,2-tirchlorethoxymethyl, any of the acetal based protecting groups, 1-ethoxyethyl, 1-(2-chloroethoxy)ethyl, 1-methyl-1-ethoxyethyl, 1-methyl-1-benzyloxyethyl, 1-methyl-1-benzyloxy-2-fluoroethyl, dihyropyranyl, methoxymethyl, 2-(phenylselenyl)ethyl, and ether based protecting groups (e.g., 2,4-dinitrophenyl ether, t-butyl ether, allyl ether, and p-methoxyphenyl ether). These embodiments for $P^1$ can be applied to any of the process or compound embodiments described infra.

In some embodiments, the deprotecting comprises treating with tetrabutylammonium fluoride. Other common methods of deprotection for specific $P^1$ protecting groups can be found in Wuts and Greene, Protective Groups in Organic Synthesis, 4th ed., John Wiley & Sons: New Jersey (2007), which is incorporated herein by reference in its entirety (in particular, see pages 16-366). In some embodiments, these deprotecting methods may apply to any of the processes described herein.

In some embodiments, the compound of Formula IV:

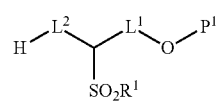

IV is prepared by a process comprising treating a compound of Formula V:

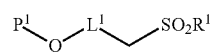

V with a strong base, followed reacting with compound of Formula VI:

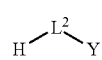

VI to form the compound of Formula IV; wherein:

P¹ is a hydroxyl protecting group;

Y is a leaving group;

L¹ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

L² is selected from $C_{4-50}$ straight-chain alkylene and $C_{4-50}$ straight-chain alkenylene; each of which is optionally substituted with 1, 2, 3, 4, 5, or 6 independently selected $R^b$ groups;

R¹ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$ alkylsulfonyl; and each $R^a$ and $R^b$ is independently selected from $C_{1-30}$ alkyl and $C_{2-30}$ alkenyl.

In some embodiments, Y is a sulfonyloxy based leaving group (e.g., p-toluenesulfonyloxy, methyl sulfonyloxy, m-nitrophenyl sulfonyloxy, p-bromophenyl sulfonyloxy, or triflate) or halogen (e.g., chloro, bromo, or iodo). In some embodiments, Y is p-toluenesulfonyloxy. In some embodiments, Y is p-toluenesulfonyloxy. In some embodiments, Y is triflate. In some embodiments, In some embodiments, Y is a leaving group found in "Advances in Organic Chemistry", J. March, 3rd Edition, Wiley Interscience, 1985, p. 310-316. In some embodiments, Y is 2-pyridylsulfenyl. In some embodiments, Y is an anion or cation based leaving groups such as —OSO₃⁻, —SSO₃⁻, —OPO₃²⁻, a phenol-based leaving group (e.g., o- or p-nitrophenol group), or Q⁺; wherein Q⁺ is NR₃⁺ (wherein R is $C_{1-20}$ alkyl group, e.g., N⁺(C₂H₄)₃) or a N-substituted heterocycle, such as pyridinium ion. These embodiments for Y can be applied to any of the process or compound embodiments described infra.

An appropriate base is one which can deprotonate the methylene group between the L¹ and SO₂R¹ groups. In some embodiments, the strong base is n-butyllithium, unstabilized lithiocarbanions (e.g., sec- or tert-butyllithium or an alkyllithium), an unhindered or hindered nitrogen based metal amide (e.g., lithium, sodium, or potassium diisopropylamide, 2,2,6,6-tetramethyl piperidide (e.g., sodium or potassium 2,2, 6,6-tetramethylpiperide) and other cyclic and acyclic metal amide bases); or a metal alkanoate (e.g., sodium or potassium tert-butoxides or tert-amyloxide in a polar aprotic solvents).

In some embodiments, the compound of Formula V:

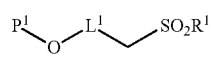

is prepared by a process comprising oxidizing a compound of Formula VII:

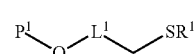

to form the compound of Formula V; wherein:

P¹ is a hydroxyl protecting group;

L¹ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

R¹ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$ alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$ alkylsulfonyl; and each $R^a$ is independently selected from $C_{1-30}$ alkyl and $C_{2-30}$ alkenyl.

In some embodiments, the oxidizing comprises treating with m-chloroperoxybenzoic acid. Examples of other oxidizing agents include, but are not limited to, oxidizing agent useful for the oxidation of sulfides to sulfones, such as (1) chromic anhydride in sulfuric acid or acetic acid; (2) peracetic acid; (3) hydrogen peroxide in the presence or absence of ZrCl₄ or with titanium catalyst; (4) peracetic acid; (5) oxone with or without tris[(2-oxazolinyl)phenolato]manganese (III); (6) sodium periodate in methanol; (7) periodic acid with cat. RuO₄ or CrO₃; (8) silica gel supported RuCl₃/NaIO₄; (9) N,N-morpholine N-oxide; (10) SeO₂ in combination with H₂O₂; (11) LDH and OsO₄; (12) N,N'-dibenzyl-N,N,N',N'-tetramethyl diammonium permanganate; (13) magnesium bis (monoperoxyphthalate) hexahydrate; or (14) potassium hydrogen persulfate and OsO₄-catalyzed oxygenation. Enzymatic oxidation methods can also be envisioned for this transformation.

In some embodiments, the compound of Formula VII:

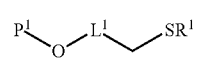

is prepared by a process comprising reacting a compound of Formula VIII:

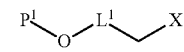

with a compound of formula R¹SH in the presence of a strong base to form the compound of Formula VII; wherein:

X is a leaving group;

P¹ is a hydroxyl protecting group;

L¹ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

R¹ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$ alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$ alkylsulfonyl; and each $R^a$ is independently selected from $C_{1-30}$ alkyl and $C_{2-30}$ alkenyl.

In some embodiments, the strong base is sodium methoxide. In some embodiments, the strong base is n-butyllithium, unstabilized lithiocarbanions (e.g., sec- or tert-butyllithium or an alkyllithium), an unhindered or hindered nitrogen based metal amide (e.g., lithium, sodium, or potassium diisopropylamide or 2,2,6,6-tetramethyl piperidide) and other cyclic and acyclic metal amide bases); or a metal alkanoate (e.g., sodium or potassium tert-butoxides or tert-amyloxide in a polar aprotic solvents).

In some embodiments, X is a sulfonyloxy based leaving group (e.g., p-toluenesulfonyloxy, methyl sulfonyloxy, m-nitrophenyl sulfonyloxy, p-bromophenyl sulfonyloxy, or triflate) or halogen (e.g., chloro, bromo, or iodo). In some embodiments, X is halogen. In some embodiments, X is bromo. These embodiments for X can be applied to any of the process or compound embodiments described infra.

In some embodiments, the compound of Formula VIII:

VIII is prepared by a process comprising protecting a compound of Formula IX:

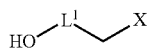

IX to form a compound of Formula VIII; wherein:
X is a leaving group;
$P^1$ is a hydroxyl protecting group;
$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
$R^1$ is phenyl, which is optionally substituted by 1, 2, 3, 4, or 5 independently selected $R^{1a}$ groups;
each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and
each $R^a$ is independently selected from $C_{1-30}$ alkyl and $C_{2-30}$ alkenyl.

Appropriate methods for protecting hydroxyl groups can be found in Wuts and Greene, Protective Groups in Organic Synthesis, 4th ed., John Wiley & Sons: New Jersey (2007), which is incorporated herein by reference in its entirety (in particular, see pages 16-366). Some appropriate $P^1$ groups are described supra. In some embodiments, these protecting methods may apply to any of the processes described herein.

In some embodiments, the compound of Formula VI:

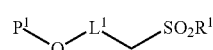

VI is prepared by a process comprising:
(a) reducing a compound of Formula X:

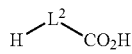

X or salt thereof, to form a compound of Formula XI:

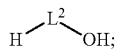

XI and
(b) converting the compound of Formula XI to the compound of Formula VI;
wherein:
Y is a leaving group;
$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups; and each $R^b$ is independently selected from $C_{1-30}$ alkyl and $C_{2-30}$ alkenyl.

In some embodiments, the reducing comprises treating with (1) lithium aluminum hydride; (2) conversion of the carboxylic acid to an acyl fluoride followed by reduction sodium borohdyride; (3) $BH_3$; (4) $BH_3.S(Me)_2$; (5) $BH_3.S(Me)_2$, $BF_3.OEt_2$; (6) $LiBH_4$, MeOH, diglyme; (7) $LiBH_4$/trimethylsilyl chloride; (8) $NaBH_4$ in the presence of $BF_3.OEt_2$ or lumina; (9) $Zn(BH_4)_2$; (10) $AlH_3$ with or without other adjuncts, such as $NMe_2Et$, $N(Et)_3$, other tertiary amine bases; (11) $LiAlH_4/AlCl_3$; $NaAlH_4$; (12) $NaH_2Al(OCH_2CH_2OCH_3)_2$; (13) $NaH_2AlEt_2$; or (14) $LiHAl(i-Bu)_2$ (n-Bu).

In some embodiments, Y is a sulfonyloxy based leaving group (e.g., p-toluenesulfonyloxy, methyl sulfonyloxy, m-nitrophenyl sulfonyloxy, p-bromophenyl sulfonyloxy, or triflate), chloro, bromo, or iodo. In some embodiments, Y is p-toluenesulfonyloxy. These embodiments for Y can be applied to any of the process or compound embodiments described infra.

The present invention further provides a compound of Formula V:

V or salt thereof; wherein:
$P^1$ is a hydroxyl protecting group;
$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
$R^1$ is phenyl, which is optionally substituted by 1, 2, 3, 4, or 5 independently selected $R^{1a}$ groups;
each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and
each $R^a$ is independently selected from $C_{1-30}$ alkyl and $C_{2-30}$ alkenyl.

In some embodiments, $P^1$ is tert-butyldimethylsilyl.

The present invention further provides a process of preparing a compound of Formula I:

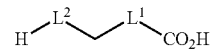

I comprising:
(a) protecting a compound of Formula IX:

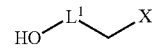

IX to form a compound of Formula VIII:

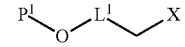

VIII (b) reacting a compound of Formula VIII with a compound of formula $R^1SH$ in the presence of sodium methoxide to form a compound of Formula VII:

VII (c) oxidizing the compound of Formula VII to form a compound of Formula V:

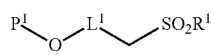

V (d) treating the compound of Formula V with n-butyllithium, followed by reacting with a compound of Formula VI:

VI to form a compound of Formula IV:

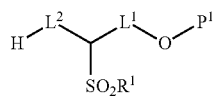

IV (e) deprotecting the compound of Formula IV to form a compound of Formula III:

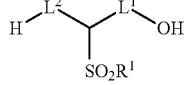

III (f) oxidizing the compound of Formula III to form a compound of Formula II:

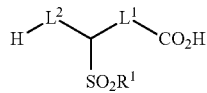

II and (g) desulfonating the compound of Formula II to form the compound of Formula I, or salt thereof;
wherein:
 $P^1$ is tert-butyldimethylsilyl;
 Y is p-toluenea sulfonyloxy;
 X is halogen;
 $L^1$ is selected from $C_{8-50}$ straight-chain alkylene and $C_{4-50}$ straight-chain alkenylene;
 $L^2$ is selected from $C_{10-50}$ straight-chain alkylene and $C_{4-50}$ straight-chain alkenylene; and
 $R^1$ is phenyl.

In some embodiments, the compound of Formula I can be prepared by the following process (e.g., Scheme 2).

Scheme 2

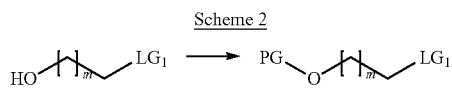

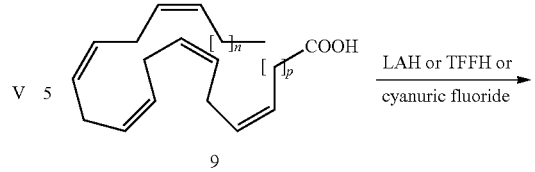

n = 1-10; p = 0-20

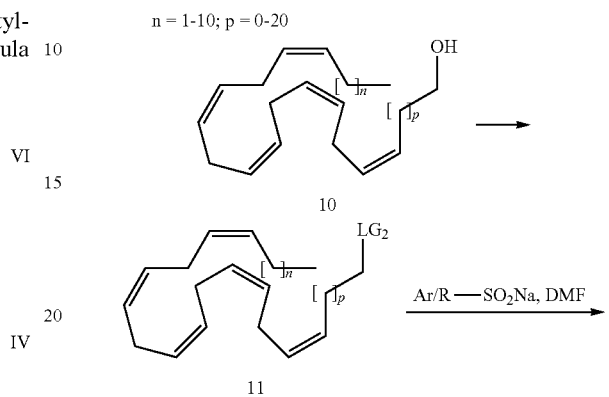

$LG_2$ = leaving group, i.e., a sulfonyl-based leaving goup (tosylate, mesylate, nosylate, brosylate etc, or a halide based leaving group

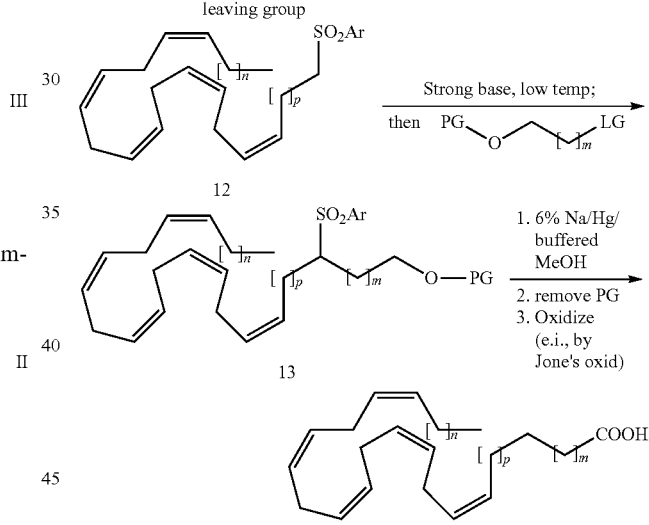

Accordingly, in some embodiments, the compound of Formula IV:

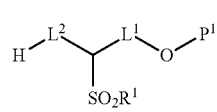

IV is prepared by a process comprising reacting a compound of Formula XII:

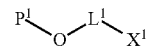

XII with a compound of Formula XIII:

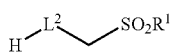

wherein:
P¹ is a hydroxyl protecting group;
X¹ is a leaving group;
L¹ is selected from C$_{4-50}$ straight-chain alkylene and C$_{4-50}$ straight-chain alkenylene; each of which is optionally substituted with 1, 2, 3, 4, 5, or 6 independently selected R$^a$ groups;
L² is selected from C$_{4-50}$ straight-chain alkylene and C$_{4-50}$ straight-chain alkenylene; each of which is optionally substituted with 1, 2, 3, 4, 5, or 6 independently selected R$^b$ groups;
R¹ is phenyl, which is optionally substituted by 1, 2, 3, 4, or 5 independently selected R$^{1a}$ groups;
each R$^{1a}$ is independently selected from halogen, cyano, nitro, hydroxyl, C$_{1-6}$ alkyl, C$_{1-6}$haloalkyl, C$_{1-6}$alkoxy, C$_{1-6}$haloalkoxy, di(C$_{1-6}$alkyl)amino, carbamyl, C$_{1-6}$ alkylcarbamyl, di(C$_{1-6}$)alkylcarbamyl, C$_{1-6}$alkoxycarbonyl, and C$_{1-6}$alkylsulfonyl; and
each R$^a$ and R$^b$ is independently selected from C$_{1-30}$ alkyl and C$_{2-30}$ alkenyl.

In some embodiments, X¹ is a sulfonyloxy based leaving group (e.g., p-toluenesulfonyloxy, methyl sulfonyloxy, m-nitrophenyl sulfonyloxy, p-bromophenyl sulfonyloxy, or triflate) or halogen (e.g., chloro, bromo, or iodo). In some embodiments, X¹ is chloro, bromo, or iodo. In some embodiments, X¹ is p-toluenesulfonyloxy. These embodiments for X¹ can be applied to any of the process or compound embodiments described infra.

In some embodiments, the compound of Formula XIII:

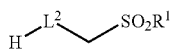

is prepared by a process comprising reacting a compound of Formula XIV:

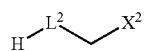

with an anion of formula R¹SO₂M to form a compound of Formula XIII;
wherein:
M is an metal counterion;
X² is a leaving group;
L² is selected from C$_{4-50}$ straight-chain alkylene and C$_{4-50}$ straight-chain alkenylene; each of which is optionally substituted with 1, 2, 3, 4, 5, or 6 independently selected R$^b$ groups;
R¹ is phenyl, which is optionally substituted by 1, 2, 3, 4, or 5 independently selected R$^{1a}$ groups;
each R$^{1a}$ is independently selected from halogen, cyano, nitro, hydroxyl, C$_{1-6}$ alkyl, C$_{1-6}$haloalkyl, C$_{1-6}$alkoxy, C$_{1-6}$haloalkoxy, di(C$_{1-6}$alkyl)amino, carbamyl, C$_{1-6}$ alkylcarbamyl, di(C$_{1-6}$)alkylcarbamyl, C$_{1-6}$alkoxycarbonyl, and C$_{1-6}$alkylsulfonyl; and
each R$^b$ is independently selected from C$_{1-30}$ alkyl and C$_{2-30}$ alkenyl.

In some embodiments, X² is a sulfonyloxy based leaving group (e.g., p-toluenesulfonyloxy, methyl sulfonyloxy, m-nitrophenyl sulfonyloxy, p-bromophenyl sulfonyloxy, or triflate) or halogen (e.g., chloro, bromo, or iodo). In some embodiments, X² is chloro, bromo, or iodo. In some embodiments, X² is p-toluenesulfonyloxy. These embodiments for X² can be applied to any of the process or compound embodiments described infra.

In some embodiments, M is an alkali metal counterion. In some embodiments, M is an sodium or lithium.

In some embodiments, the compound of Formula XIV:

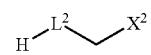

is prepared by a process comprising converting a compound of Formula XV:

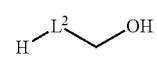

to a compound of Formula XIV; wherein:
X² is a leaving group;
L² is selected from C$_{4-50}$ straight-chain alkylene and C$_{4-50}$ straight-chain alkenylene; each of which is optionally substituted with 1, 2, 3, 4, 5, or 6 independently selected R$^b$ groups; and
each R$^b$ is independently selected from C$_{1-30}$ alkyl and C$_{2-30}$ alkenyl.

In some embodiments, the compound of Formula XV:

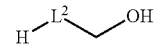

is prepared by a process comprising reducing a compound of Formula XVI:

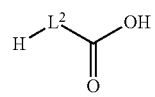

to form a compound of Formula XV; wherein:
L² is selected from C$_{4-50}$ straight-chain alkylene and C$_{4-50}$ straight-chain alkenylene; each of which is optionally substituted with 1, 2, 3, 4, 5, or 6 independently selected R$^b$ groups; and
each R$^b$ is independently selected from C$_{1-30}$ alkyl and C$_{2-30}$ alkenyl.

In some embodiments, the reducing comprises treating with lithium aluminum hydride. In some embodiments, the reducing comprises the reagents described previously.

In some embodiments, the compound of Formula XIII:

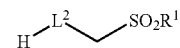

is prepared by a process comprising oxidizing a compound of Formula XVIII:

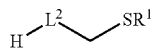
XVIII wherein:

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$ alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and each $R^b$ is independently selected from $C_{1-30}$ alkyl and $C_{2-30}$ alkenyl.

In some embodiments, the oxidizing comprises treating with m-chloroperoxybenzoic acid. In some embodiments, the oxidizing comprises a reagent described previously for the oxidation of sulfides to sulfones.

In some embodiments, the compound of Formula XVIII:

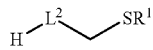
XVIII is prepared by a process comprising reacting a compound of Formula XIV:

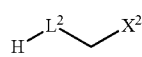
XIV with a compound of formula $R^1SH$ in the presence of a strong base; wherein:

$X^2$ is a leaving group;

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and each $R^b$ is independently selected from $C_{1-30}$ alkyl and $C_{2-30}$ alkenyl.

In some embodiments, the strong base is sodium methoxide or n-butyllithium. In some embodiments, the strong base is one of the strong bases described previously.

The compound of Formula XIV may be synthesized as summarized supra.

In some embodiments, the compound of Formula I:

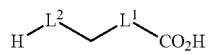
I or salt thereof, is prepared by a process comprising:

(a) reducing a compound of Formula XVI:

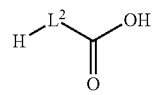
XVI to form a compound of Formula XV:

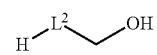
XV (b) converting the compound of Formula XV to a compound of Formula XIV:

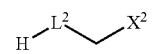
XIV (c) reacting the compound of Formula XIV with an anion of formula $R^1SO_2M$ to form a compound of Formula XIII:

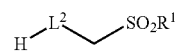
XIII (d) treating the compound of Formula XIII with a strong base, followed by reacting with a compound of Formula XII:

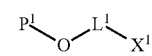
XII to form a compound of Formula IV:

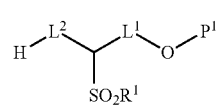
IV (e) desulfonating the compound of Formula IV to form a compound of Formula XVIa:

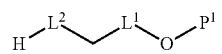
XVIa (f) deprotecting the compound of Formula XVIa:

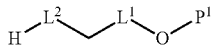

XVIa to form a compound of Formula XVII:

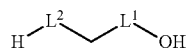

XVII and (g) oxidizing the compound of Formula XVII:

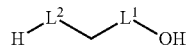

XVII to form the compound of Formula I, or salt thereof;

P¹ is a hydroxyl protecting group;

X² and X¹ are each, independently, a leaving group;

L¹ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

L² is selected from $C_{4-50}$ straight-chain alkylene and $C_{4-50}$ straight-chain alkenylene; each of which is optionally substituted with 1, 2, 3, 4, 5, or 6 independently selected $R^b$ groups;

R¹ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$ alkoxycarbonyl, and $C_{1-6}$alkylsulfonyl; and each $R^a$ and $R^b$ is independently selected from $C_{1-30}$ alkyl and $C_{2-30}$ alkenyl.

In some embodiments, the compound of Formula I:

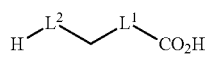

I is prepared by a process comprising:

(a) reducing a compound of Formula XVI:

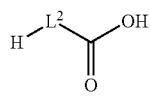

XVI to form a compound of Formula XV:

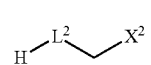

XV (b) converting the compound of Formula XV to a compound of Formula XIV:

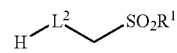

XIV (c) reacting the compound of Formula XIV with an anion of formula $R^1SO_2M$ to form a compound of Formula XIII:

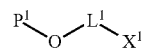

XIII (d) treating the compound of Formula XIII with a strong base, followed by reacting with a compound of Formula XII:

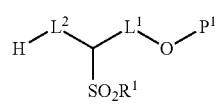

XII to form a compound of Formula IV:

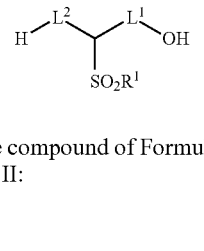

IV (e) deprotecting the compound of Formula IV to form a compound of Formula III:

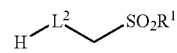

III (f) oxidizing the compound of Formula III to form a compound of Formula II:

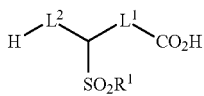

II and (g) desulfonating the compound of Formula II to form the compound of Formula I, or salt thereof;

P¹ is a hydroxyl protecting group;

X² and X¹ are each, independently, a leaving group;

L¹ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

L² is selected from $C_{4-50}$ straight-chain alkylene and $C_{4-50}$ straight-chain alkenylene; each of which is optionally substituted with 1, 2, 3, 4, 5, or 6 independently selected $R^b$ groups;

R¹ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and each $R^a$ and $R^b$ is independently selected from $C_{1-30}$ alkyl and $C_{2-30}$ alkenyl.

Particular oxidizing and desulfonating conditions are described supra. Particular strong bases are described supra.

In some embodiments, the compound of Formula I can also be formed by the following process steps (e.g., Scheme 3 or 4).

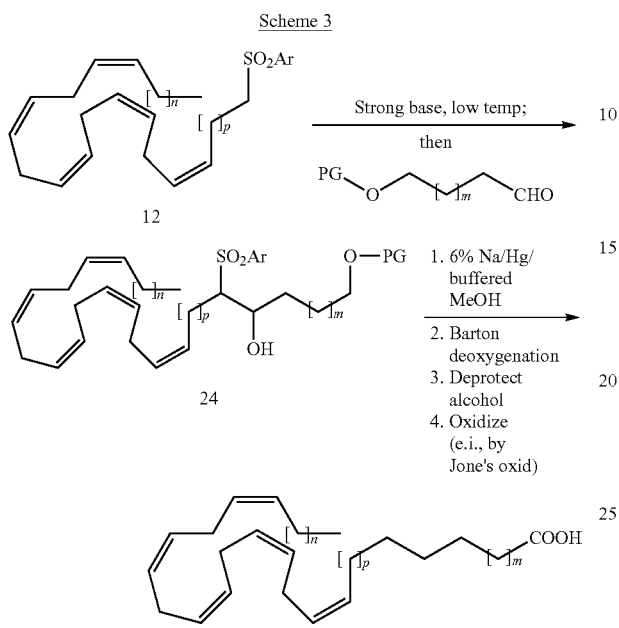

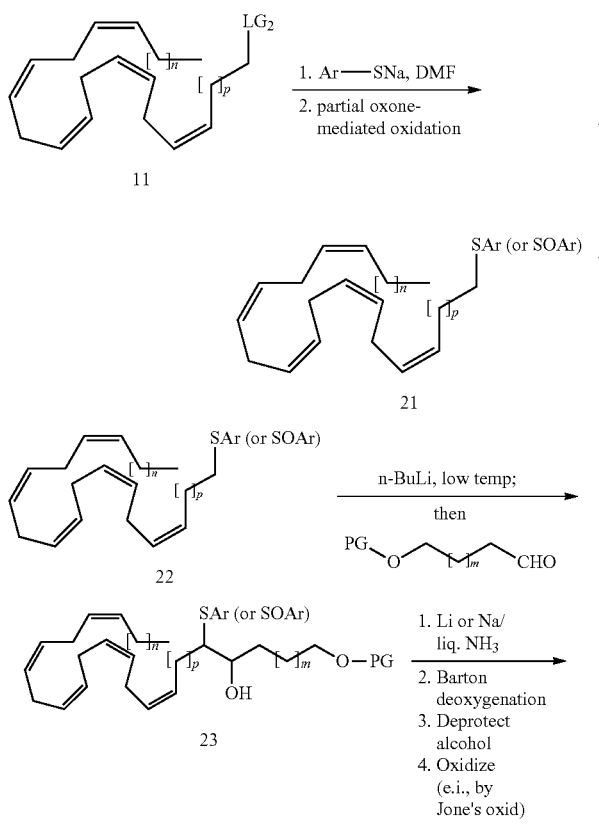

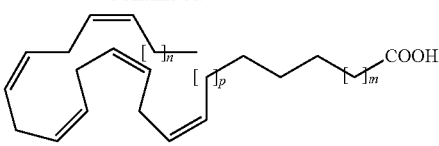

Accordingly, a compound of Formula XXI:

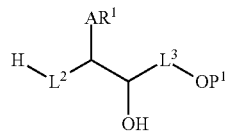
XXI is prepared by a process comprising reacting a compound of Formula XVIII:

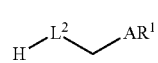
XVIII with a strong base, followed by reacting with a compound of Formula XXII:

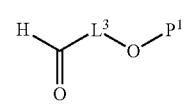
XXII to form a compound of Formula XXI;

wherein:

A is —S— or —S(O)$_2$—;

P$^1$ is a hydroxyl protecting group;

L$^1$ is —CH$_2$-L$^3$-;

L$^3$ is selected from C$_{3-50}$ straight-chain alkylene and C$_{3-50}$ straight-chain alkenylene; each of which is optionally substituted with 1, 2, 3, 4, 5, or 6 independently selected R$^a$ groups;

L$^2$ is selected from C$_{4-50}$ straight-chain alkylene and C$_{4-50}$ straight-chain alkenylene; each of which is optionally substituted with 1, 2, 3, 4, 5, or 6 independently selected R$^b$ groups;

R$^1$ is phenyl, which is optionally substituted by 1, 2, 3, 4, or 5 independently selected R$^{1a}$ groups;

each R$^{1a}$ is independently selected from halogen, cyano, nitro, hydroxyl, C$_{1-6}$ alkyl, C$_{1-6}$haloalkyl, C$_{1-6}$alkoxy, C$_{1-6}$haloalkoxy, di(C$_{1-6}$alkyl)amino, carbamyl, C$_{1-6}$ alkylcarbamyl, di(C$_{1-6}$)alkylcarbamyl, C$_{1-6}$alkoxycarbonyl, and C$_{1-6}$alkylsulfonyl; and each R$^a$ and R$^b$ is independently selected from C$_{1-30}$ alkyl and C$_{2-30}$ alkenyl.

In some embodiments, the strong base is n-butyllithium. In some embodiments, the strong base is one of the strong bases described previously.

Appropriate P$^1$ groups are described supra.

In some embodiments, the compound of Formula XXI is a compound of Formula XXIa:

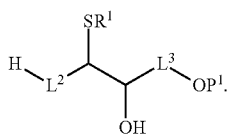

In some embodiments, the compound of Formula XXI is a compound of Formula XX:

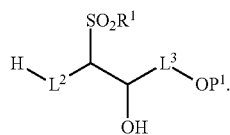

In some embodiments, the process further comprises oxidizing the compound of Formula XVII:

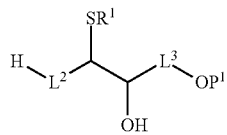

to a compound of Formula XXIb:

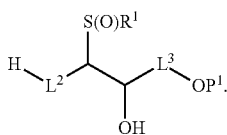

In some embodiments, the oxidizing comprises oxone-mediated oxidation. In some embodiments, the oxidizing comprises one of the methods of oxidizing a sulfide to sulfone described previously.

In some embodiments, the process further comprises desulfonating a compound of Formula XX:

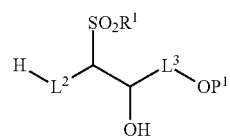

to form a compound of Formula XIX:

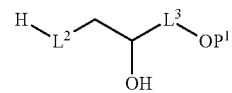

wherein:

$P^1$ is a hydroxyl protecting group;

$L^1$ is —$CH_2$-$L^3$-;

$L^3$ is selected from $C_{3-50}$ straight-chain alkylene and $C_{3-50}$ straight-chain alkenylene; each of which is optionally substituted with 1, 2, 3, 4, 5, or 6 independently selected $R^a$ groups;

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and each $R^a$ and $R^b$ is independently selected from $C_{1-30}$ alkyl and $C_{2-30}$ alkenyl.

Appropriate desulfonation routes are described supra.

In some embodiments, the process further comprises reducing a compound of Formula XXIa or XXIb:

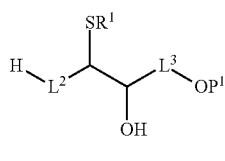

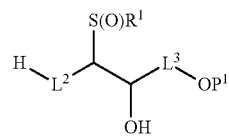

to form a compound of Formula XIX:

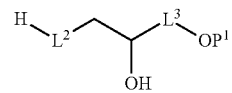

wherein:

$P^1$ is a hydroxyl protecting group;

$L^1$ is —$CH_2$-$L^3$-;

$L^3$ is selected from $C_{3-50}$ straight-chain alkylene and $C_{3-50}$ straight-chain alkenylene; each of which is optionally substituted with 1, 2, 3, 4, 5, or 6 independently selected $R^a$ groups;

$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;

$R^1$ is phenyl, which is optionally substituted by 1, 2, 3, 4, or 5 independently selected $R^{1a}$ groups;

each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$ haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and each $R^a$ and $R^b$ is independently selected from $C_{1-30}$ alkyl and $C_{2-30}$ alkenyl.

In some embodiments, the reducing comprises reacting with lithium or sodium in liquid ammonia. In some embodiments, the reducing comprises one of the methods of reducing described previously.

In some embodiments, the process further comprises deoxygenating a compound of Formula XIX:

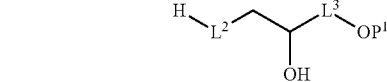

to form a compound of Formula XVIa:

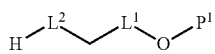

wherein

P$^1$ is a hydroxyl protecting group;

L$^1$ is —CH$_2$-L$^3$-;

L$^3$ is selected from C$_{3-50}$ straight-chain alkylene and C$_{3-50}$ straight-chain alkenylene; each of which is optionally substituted with 1, 2, 3, 4, 5, or 6 independently selected R$^a$ groups;

L$^2$ is selected from C$_{4-50}$ straight-chain alkylene and C$_{4-50}$ straight-chain alkenylene; each of which is optionally substituted with 1, 2, 3, 4, 5, or 6 independently selected R$^b$ groups; and each R$^a$ and R$^b$ is independently selected from C$_{1-30}$ alkyl and C$_{2-30}$ alkenyl.

In some embodiments, the deoxygenating comprises a Barton deoxygenation process. In some embodiments, the deoxygenating comprises: (1) tosylation, methylation, or nosylation of the alcohol followed by reduction with a strong metal hydride (e.g., lithium aluminum hydride, BH$_3$.THF); (2) conversion to a halide by any of the known methods (e.g., chloride, bromide, or iodide formation using reagents, such as, CBr$_4$/Ph$_3$P, or CBr$_4$/N-bromosuccinimide or tosylation/mesylation followed NaI treatment), followed by reduction with tri-n-butyltin hydride); or (3) conversion of the alcohol to a tolylate or mesylate followed by reaction with 2-pyridyl mercaptan to give the 2-pyridyl lipid sulfide which is then removed with Na—Hg in the usual manner.

The compound of Formula XVIa can then be converted to a compound of Formula I by the processes described supra. The compounds of Formula XIII and XVII may be prepared as described supra.

In some embodiments, the compound of Formula I can be formed by the following process steps (e.g., Scheme 5).

Scheme 5

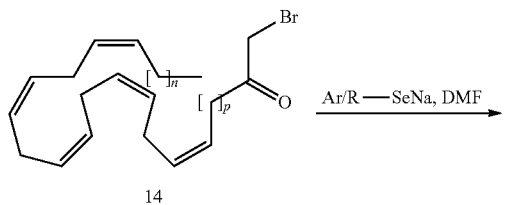

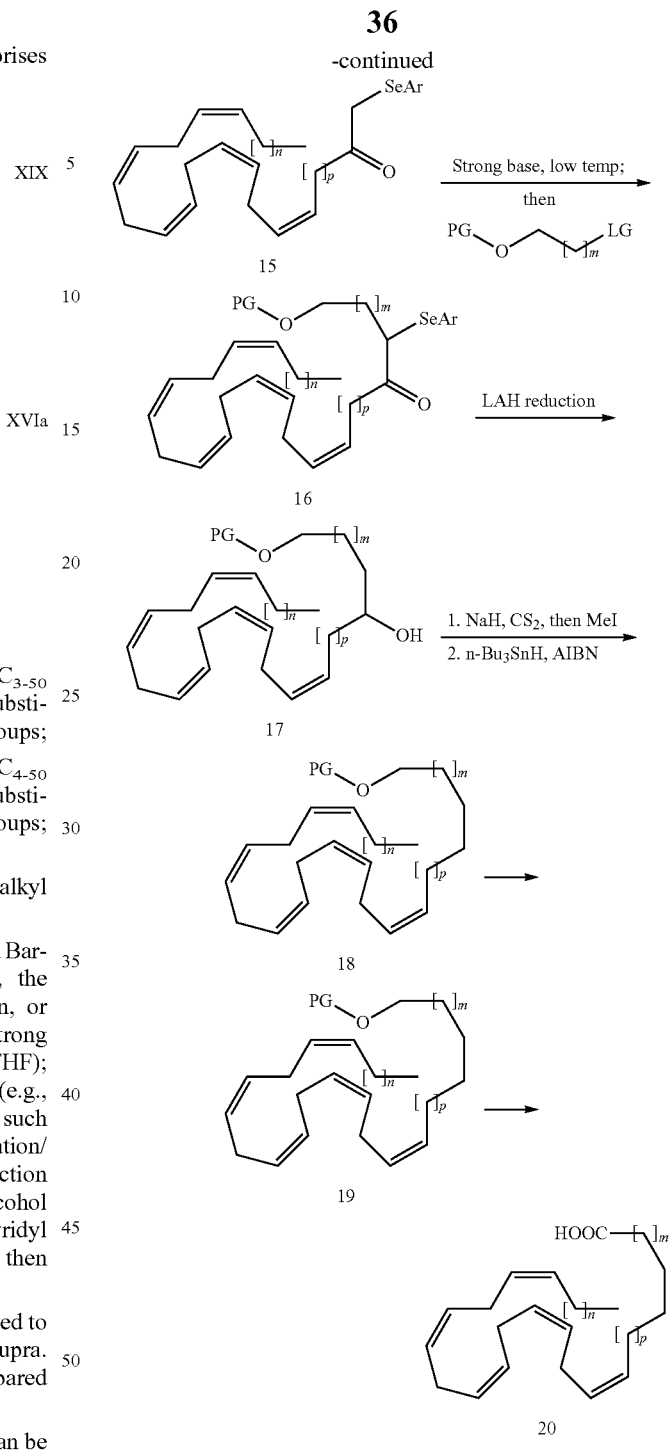

Accordingly, in some embodiments, a compound of Formula XXIV:

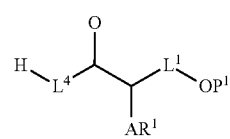

is prepared by a process comprising reacting a compound of Formula XXIII:

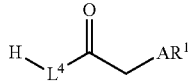
XXIII with a strong base, followed by reacting with a compound of Formula XII:

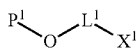
XII to form a compound of Formula XXIV; wherein:
$P^1$ is a hydroxyl protecting group;
$X^1$ is a leaving group;
A is —Se—, —S—, —S(O)— or —S(O)$_2$—;
$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
$L^2$ is -$L^4$-CH$_2$—;
$L^4$ is selected from $C_{3-50}$ straight-chain alkylene and $C_{3-50}$ straight-chain alkenylene; each of which is optionally substituted with 1, 2, 3, 4, 5, or 6 independently selected $R^b$ groups;
$R^1$ is phenyl, which is optionally substituted by 1, 2, 3, 4, or 5 independently selected $R^{1a}$ groups;
each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$ haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and
each $R^a$ and $R^b$ is independently selected from $C_{1-30}$ alkyl and $C_{2-30}$ alkenyl.

In some embodiments, A is —Se—. In some embodiments, A is —S—. In some embodiments, A is —S(O)$_2$—. In some embodiments, A is —S(O)—.

An appropriate base is one which can deprotonate the methylene group between the C(=O) and AR$^1$ groups. In some embodiments, the strong base is a metal alkoxides and metal amides as described previously. In some embodiments, the base is one of the strong bases described previously.

In some embodiments, the compound of Formula XXIII:

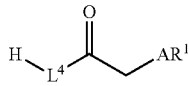
XXIII is formed by a process comprising reacting a compound of Formula XXIIIa:

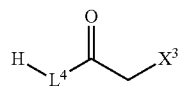
XXIIIa with an anion of formula R$^1$A- to form the compound of Formula XXIII; wherein:
$X^3$ is a leaving group;
A is —Se—, —S—, —S(O)— or —S(O)$_2$—;
$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
$L^2$ is -$L^4$-CH$_2$—;
$L^4$ is selected from $C_{3-50}$ straight-chain alkylene and $C_{3-50}$ straight-chain alkenylene; each of which is optionally substituted with 1, 2, 3, 4, 5, or 6 independently selected $R^b$ groups;
$R^1$ is phenyl, which is optionally substituted by 1, 2, 3, 4, or 5 independently selected $R^{1a}$ groups;
each $R^{1a}$ is independently selected from halogen, cyano, nitro, hydroxyl, $C_{1-6}$ alkyl, $C_{1-6}$ haloalkyl, $C_{1-6}$ alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and
each $R^a$ and $R^b$ is independently selected from $C_{1-30}$ alkyl and $C_{2-30}$ alkenyl.

In some embodiments, A is —Se—. In some embodiments, A is —S—. In some embodiments, A is —S(O)$_2$—. In some embodiments, A is —S(O)—.

In some embodiments, $X^3$ is a sulfonyloxy based leaving group (e.g., p-toluenesulfonyloxy, methyl sulfonyloxy, m-nitrophenyl sulfonyloxy, p-bromophenyl sulfonyloxy, or triflate) or halogen (e.g., chloro, bromo, or iodo). In some embodiments, $X^3$ is chloro, bromo, or iodo. $X^3$ is bromo. In some embodiments, $X^1$ is p-toluenesulfonyloxy. These embodiments for $X^3$ can be applied to any of the process or compound embodiments described infra.

In some embodiments, the process further comprises desulfonating or reducing the compound of Formula XXIV:

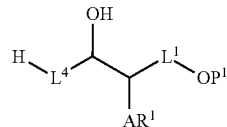
XXIV to form a compound of Formula XXV:

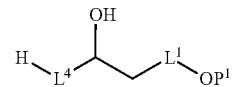
XXV wherein:
$P^1$ is a hydroxyl protecting group;
A is —Se—, —S—, —S(O)— or —S(O)$_2$—;
$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
$L^2$ is -$L^4$-CH$_2$—;
$L^4$ is selected from $C_{3-50}$ straight-chain alkylene and $C_{3-50}$ straight-chain alkenylene; each of which is optionally substituted with 1, 2, 3, 4, 5, or 6 independently selected $R^b$ groups;
$R^1$ is phenyl, which is optionally substituted by 1, 2, 3, 4, or 5 independently selected $R^{1a}$ groups;
each $R^{1a}$ is independently selected from halogen, cyano, nitro, hydroxyl, $C_{1-6}$ alkyl, $C_{1-6}$haloalkyl, $C_{1-6}$alkoxy, $C_{1-6}$haloalkoxy, di($C_{1-6}$alkyl)amino, carbamyl, $C_{1-6}$ alkylcarbamyl, di($C_{1-6}$)alkylcarbamyl, $C_{1-6}$alkoxycarbonyl, and $C_{1-6}$alkylsulfonyl; and
each $R^a$ and $R^b$ is independently selected from $C_{1-30}$ alkyl and $C_{2-30}$ alkenyl.

In some embodiments, A is —Se—. In some embodiments, A is —S—. In some embodiments, A is —S(O)$_2$—. In some embodiments, A is —S(O)—.

In some embodiments, the desulfonating comprises treating with sodium-mercury amalgam. In some embodiment, the desulfonating comprises one of the methods of desulfonation described previously.

In some embodiments, the reducing comprises reacting with lithium or sodium in liquid ammonia. In some embodiments, the reducing comprises treating with sodium hydride, carbon disulfide, and then methyl iodide, followed by treatment with tri(n-butyl)tin in the presence of AIBN (Barton deoxygenation). In some embodiments, the reducing may be any of the deoxygenation methods described previously.

In some embodiments, the process further comprises deoxygenating the compound of Formula XXV:

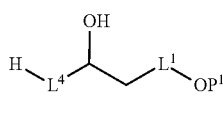

XXV to form a compound of Formula XVIa:

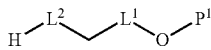

XVIa wherein:

P$^1$ is a hydroxyl protecting group;

L$^1$ is selected from C$_{4-50}$ straight-chain alkylene and C$_{4-50}$ straight-chain alkenylene; each of which is optionally substituted with 1, 2, 3, 4, 5, or 6 independently selected R$^a$ groups;

L$^2$ is -L$^4$-CH$_2$—;

L$^4$ is selected from C$_{3-50}$ straight-chain alkylene and C$_{3-50}$ straight-chain alkenylene; each of which is optionally substituted with 1, 2, 3, 4, 5, or 6 independently selected R$^b$ groups; and each R$^a$ and R$^b$ is independently selected from C$_{1-30}$ alkyl and C$_{2-30}$ alkenyl.

In some embodiments, the deoxygenating comprises a Barton deoxygenation process. In some embodiments, the deoxygenating comprises one of the deoxygenation methods described previously.

The compound of Formula XVIa can then be converted to a compound of Formula I by the processes described supra.

In some embodiments, the compound of Formula I can be formed by the following process steps (e.g., Scheme 6).

Scheme 6

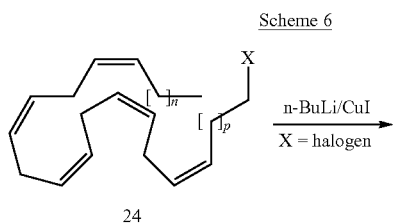

24

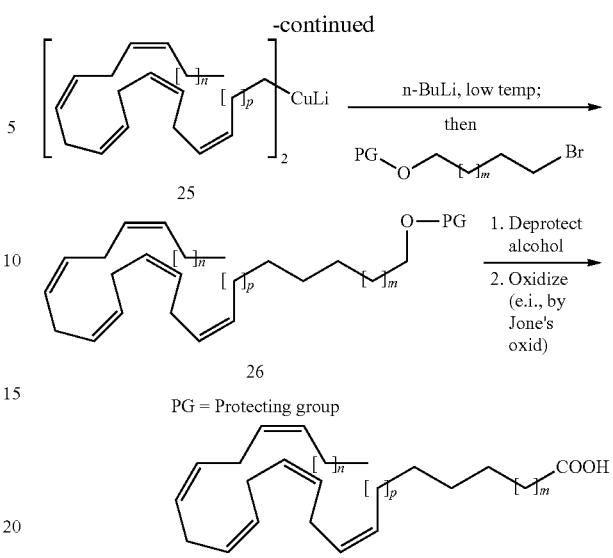

PG = Protecting group

Accordingly, in some embodiments, a compound of Formula XVIa:

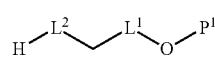

XVIa is prepared by a process comprising reacting a compound of Formula XXVI:

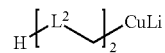

XXVI with a compound of Formula XII:

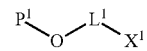

XII to form a compound XVIa; wherein:

X$^1$ is halogen;

P$^1$ is a hydroxyl protecting group;

L$^1$ is selected from C$_{4-50}$ straight-chain alkylene and C$_{4-50}$ straight-chain alkenylene; each of which is optionally substituted with 1, 2, 3, 4, 5, or 6 independently selected R$^a$ groups;

L$^2$ is -L$^4$-CH$_2$—;

L$^4$ is selected from C$_{3-50}$ straight-chain alkylene and C$_{3-50}$ straight-chain alkenylene; each of which is optionally substituted with 1, 2, 3, 4, 5, or 6 independently selected R$^b$ groups; and each R$^a$ and R$^b$ is independently selected from C$_{1-30}$ alkyl and C$_{2-30}$ alkenyl.

In some embodiments, X$^1$ is chloro, bromo, or iodo. X$^1$ is bromo.

The compound of Formula XVIa may be converted to a compound of Formula I as described supra.

In some embodiments, the compound of Formula XXVI:

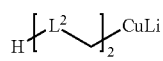
XXVI is prepared by a process comprising treating a compound of Formula XIV:

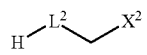
XIV with a strong base, followed by reacting with copper(I) iodide; wherein:

$X^2$ is a leaving group;

$L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;

$L^2$ is -$L^4$-$CH_2$—;

$L^4$ is selected from $C_{3-50}$ straight-chain alkylene and $C_{3-50}$ straight-chain alkenylene; each of which is optionally substituted with 1, 2, 3, 4, 5, or 6 independently selected $R^b$ groups; and each $R^a$ and $R^b$ is independently selected from $C_{1-30}$ alkyl and $C_{2-30}$ alkenyl.

In some embodiments, the strong base is n-butyllithium. In some embodiments, the strong base is one of the strong bases described previously. Other strong halogen-metal exchange reagents can be sec- or tert. butyllithium or any other alkyllithium, or pure alkali or alkaline earth metals (Li, Na, K, or Mg) base.

In some embodiments, the compound of Formula I can be prepared by the following process steps (see e.g., Scheme 7).

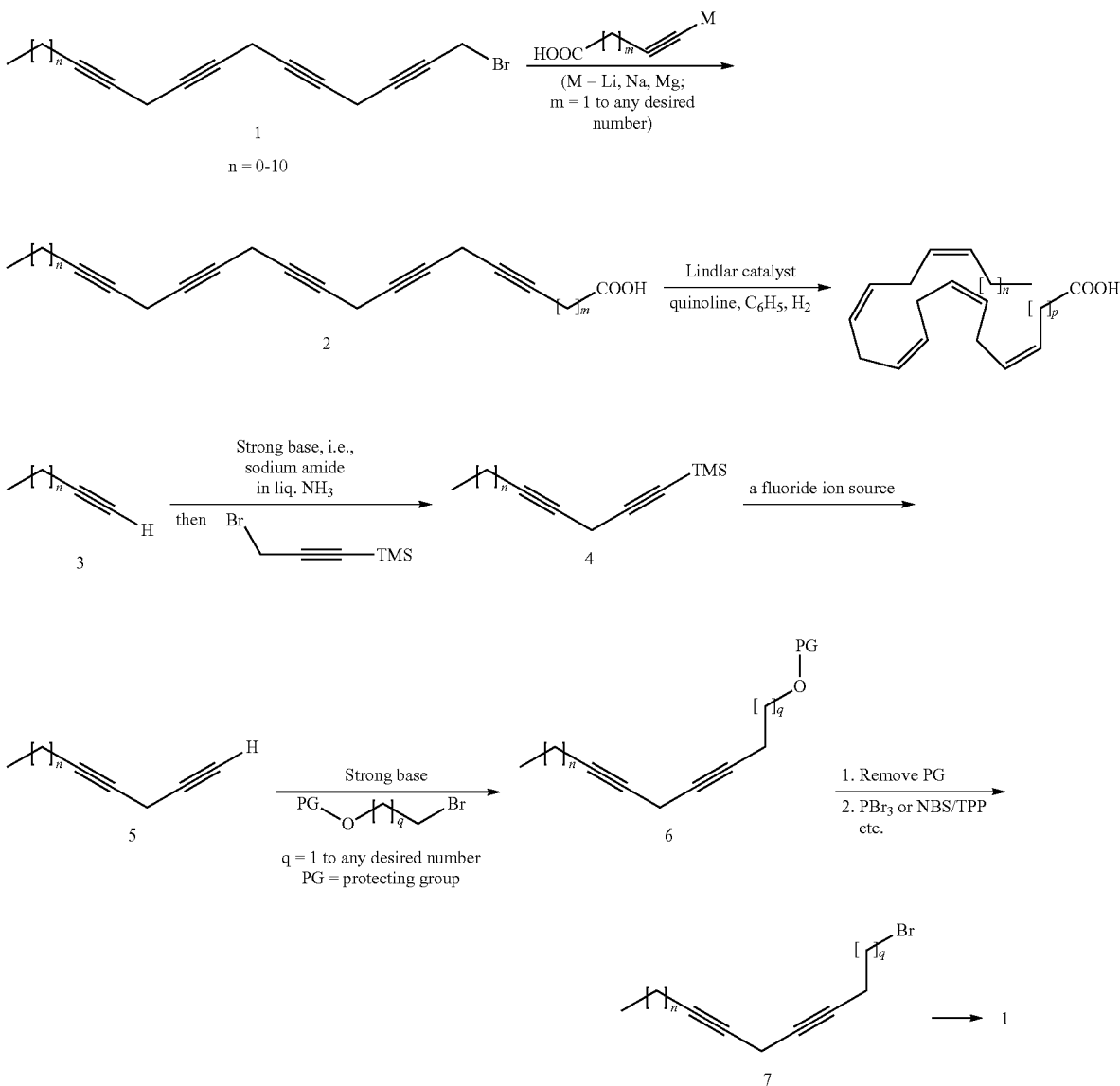

Accordingly, in some embodiments, a compound of Formula I:

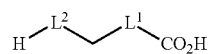

is prepared by a process comprising reducing a compound of Formula XXVII:

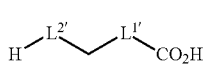

wherein:
$L^1$ is selected from $C_{4-60}$ straight-chain alkylene and $C_{4-60}$ straight-chain alkenylene; which is optionally substituted with 1, 2, 3, 4, 5, or 6 independently selected $R^a$ groups;
$L^2$ is selected from $C_{4-60}$ straight-chain alkylene and $C_{4-60}$ straight-chain alkenylene; which is optionally substituted with 1, 2, 3, 4, 5, or 6 independently selected $R^b$ groups;
$L^{1'}$ is $C_{4-60}$ straight-chain alkynylene; which is optionally substituted with 1, 2, 3, 4, 5, or 6 independently selected $R^c$ groups;
$L^{2'}$ is $C_{4-60}$ straight-chain alkynylene; which is optionally substituted with 1, 2, 3, 4, 5, or 6 independently selected $R^d$ groups;
each $R^a$ and $R^b$ is independently selected from $C_{1-30}$ alkyl and $C_{2-30}$ alkenyl; and
each $R^c$ and $R^d$ is independently selected from $C_{1-30}$ alkyl, $C_{2-30}$ alkenyl, and $C_{2-30}$ alkynyl.

In some embodiments, the reducing comprises treating with hydrogen gas in the presence of Lindlar catalyst. In some embodiments, the reducing results in complete saturation ($L^1$ and $L^2$ being alkylene groups). In some embodiments, the reducing results in $L^1$ and/or $L^2$ being alkenylene groups.

In some embodiments, the compound of Formula XXVII is a compound of Formula Ia:

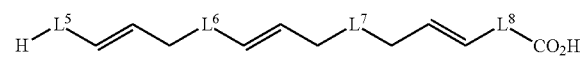

and the compound of Formula XXVII is a compound of Formula XXVIIa:

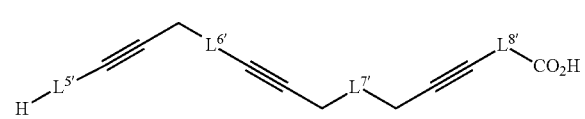

wherein:
$L^5$, $L^6$, $L^7$, and $L^8$ are each independently selected from $C_{2-25}$ straight-chain alkylene and $C_{2-25}$ straight-chain alkenylene; and
$L^{5'}$, $L^{6'}$, $L^{7'}$, and $L^{8'}$ are each independently selected from $C_{2-25}$ straight-chain alkylene, $C_{2-25}$ straight-chain alkenylene, and $C_{2-25}$ straight-chain alkynylene.

While Formula Ia shows trans-double bonds, the double-bonds may be either trans or cis. In some embodiments, the double-bonds are all trans. In some embodiments, the double-bonds are all cis.

In some embodiments, the compound of Formula XXVIIa:

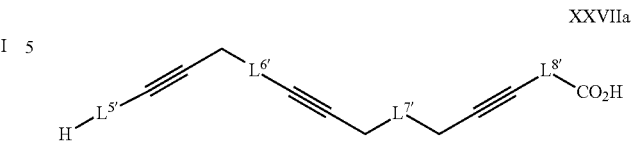

is prepared by a process comprising reacting a compound of Formula XXVIII:

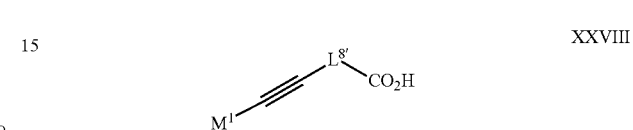

with a compound of Formula XXIX:

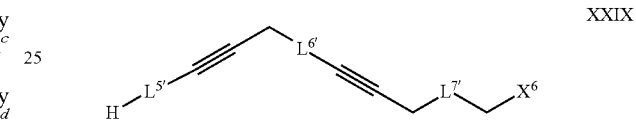

wherein:
$X^6$ is halogen;
$M^1$ is an alkali metal metal counterion;
$L^5$, $L^6$, $L^7$, and $L^8$ are each independently selected from $C_{2-25}$ straight-chain alkylene and $C_{2-25}$ straight-chain alkenylene; and
$L^{5'}$, $L^{6'}$, $L^{7'}$, and $L^{8'}$ are each independently selected from $C_{2-25}$ straight-chain alkylene, $C_{2-25}$ straight-chain alkenylene, and $C_{2-25}$ straight-chain alkynylene.

In some embodiments, $X^6$ is chloro, bromo or iodo. In some embodiments, $X^6$ is bromo. These embodiments for $X^6$ can be applied to any of the process or compound embodiments described infra.

In some embodiments, $M^1$ is lithium. In some embodiments, $M^1$ is sodium. In some embodiments, $M^1$ is lithium or sodium. These embodiments for $M^1$ can be applied to any of the process or compound embodiments described infra.

In some embodiments, the compound of Formula XXIX:

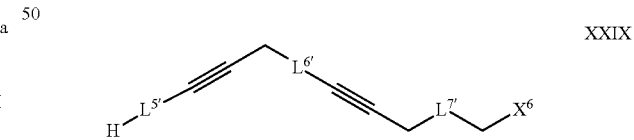

is prepared by a process comprising:
(a) deprotecting a compound of Formula XXX:

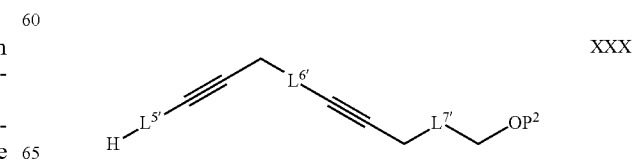

to form a compound of Formula XXXI:

XXXI

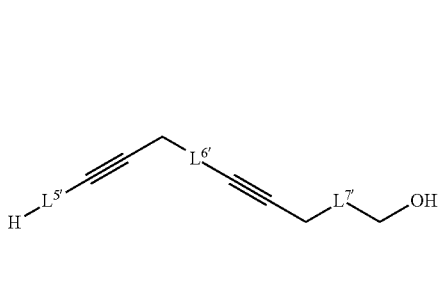

(b) halogenating the compound of Formula XXXI to form the compound of Formula XXIX; wherein:

P² is a hydroxyl protecting group;

$L^5$, $L^6$, $L^7$, and $L^8$ are each independently selected from $C_{2-25}$ straight-chain alkylene and $C_{2-25}$ straight-chain alkenylene; and $L^{5'}$, $L^{6'}$, $L^{7'}$, and $L^{8'}$ are each independently selected from $C_{2-25}$ straight-chain alkylene, $C_{2-25}$ straight-chain alkenylene, and $C_{2-25}$ straight-chain alkynylene.

Appropriate P² hydroxyl protecting groups include, but are not limited to the protecting groups for hydroxyl groups delineated in Wuts and Greene, Protective Groups in Organic Synthesis, 4th ed., John Wiley & Sons: New Jersey (2007), which is incorporated herein by reference in its entirety (in particular, those at pages 16-366). In some embodiments, P² is a silyl ether. In some embodiments, P² is trimethylsilyl, triisopropylsilyl, dimethylisopropylsilyl, diethylisopropylsilyl, dimethylthexylsilyl, 2-norbornyldimethylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, bis-(tert-butyl)-1-pyrenylmethoxysilyl, tris(trimethylsilyl)silyl(sisyl), (2-hydroxystyryl)dimethylsilyl, (2-hydroxystyryl)diisopropylsilyl, tert-butylmethoxyphenylsilyl, tert-butoxydiphenylsilyl, 1,1,3,3-tetraisopropyl-3-[2-(triphenylmethoxy)ethoxy)disiloxane-1-yl) or fluorous silyl. P² is tert-butyldimethylsilyl. In some embodiments, P² is tert-butyldiphenylsilyl. In some embodiments, the protecting group is trimethylsiylethoxymethyl, 2-trimethylsilyethyl, p-methoxybenzyl, 3,4-dimethoxybenzyl, 2,2,2-tirchlorethoxymethyl, any of the acetal based protecting groups, 1-ethoxyethyl, 1-(2-chloroethoxy)ethyl, 1-methyl-1-ethoxyethyl, 1-methyl-1-benzyloxyethyl, 1-methyl-1-benzyloxy-2-fluoroethyl, dihyropyranyl, methoxymethyl, 2-(phenylselenyl)ethyl, and ether based protecting groups (e.g., 2,4-dinitrophenyl ether, t-butyl ether, allyl ether, and p-methoxyphenyl ether). These embodiments for P² can be applied to any of the process or compound embodiments described infra.

Common methods of deprotection for specific P² hydroxyl protecting groups can be found in Wuts and Greene, Protective Groups in Organic Synthesis, 4th ed., John Wiley & Sons: New Jersey (2007), which is incorporated herein by reference in its entirety (in particular, see pages 16-366). In some embodiments, these deprotecting methods may apply to any of the processes described herein.

In some embodiments, the halogenating comprises treating with $P(X^6)_3$ or N-halosuccinimide. In some embodiments, the halogenating comprises treating with $PBr_3$ or N-bromosuccinimide.

In some embodiments, the compound of Formula XXXI:

XXX

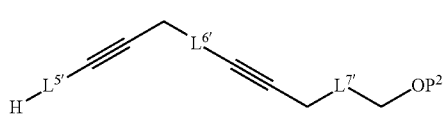

is prepared by a process comprising treating a compound of Formula XXXII:

XXXII

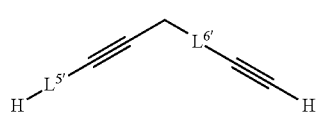

with a strong base, followed by reacting with a compound of Formula XXXIII:

XXXIII

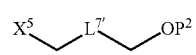

to form the compound of Formula XXX; wherein:

P² is a hydroxyl protecting group;

$X^5$ is a leaving group;

$L^5$, $L^6$, $L^7$, and $L^8$ are each independently selected from $C_{2-25}$ straight-chain alkylene and $C_{2-25}$ straight-chain alkenylene; and $L^{5'}$, $L^{6'}$, $L^{7'}$, and $L^{8'}$ are each independently selected from $C_{2-25}$ straight-chain alkylene, $C_{2-25}$ straight-chain alkenylene, and $C_{2-25}$ straight-chain alkynylene.

In some embodiments, $X^5$ is a sulfonyloxy based leaving group (e.g., p-toluenesulfonyloxy, methyl sulfonyloxy, m-nitrophenyl sulfonyloxy, p-bromophenyl sulfonyloxy, or triflate), chloro, bromo, or iodo. $X^5$ is chloro, bromo, or iodo. In some embodiments, $X^5$ is bromo. In some embodiments, $X^5$ is one of the leaving groups described previously for Y. These embodiments for $X^5$ can be applied to any of the process or compound embodiments described infra.

In some embodiments, the strong base is n-butyllithium. In some embodiments, the strong base is sodium amide. In some embodiments, the strong base is one of the strong bases described previously.

In some embodiments, the compound of Formula XXXII:

XXXII is prepared by a process comprising reacting a compound of Formula XXXIV:

XXXIV with a source of fluoride to form the compound of Formula XXXII; wherein:

each $R^e$ is, independently, $C_{1-4}$ alkyl;

$L^5$, $L^6$, $L^7$, and $L^8$ are each independently selected from $C_{2-25}$ straight-chain alkylene and $C_{2-25}$ straight-chain alkenylene; and $L^{5'}$, $L^{6'}$, $L^{7'}$, and $L^{8'}$ are each independently selected from $C_{2-25}$ straight-chain alkylene, $C_{2-25}$ straight-chain alkenylene, and $C_{2-25}$ straight-chain alkynylene.

In some embodiments, $R^e$ is methyl. In some embodiments, the source of fluoride is teta-n-butylammonium fluoride that is used in the tetrahydrofuran solvent. Hydrogen fluoride or other metal fluorides like sodium, potassium or magnesium/calcium fluoride can also be used.

In some embodiments, the compound of Formula XXXIV:

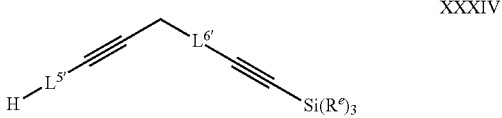

XXXIV is prepared by a process comprising treating a compound of Formula XXXV:

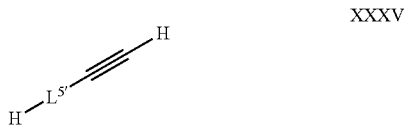

XXXV with a strong base, followed by reacting with a compound of Formula XXXVI:

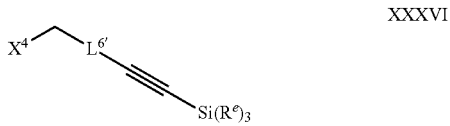

XXXVI to form the compound of Formula XXXIV; wherein:
$X^4$ is a leaving group;
each $R^e$ is, independently, $C_{1-4}$ alkyl;
$L^5$, $L^6$, $L^7$, and $L^8$ are each independently selected from $C_{2-25}$ straight-chain alkylene and $C_{2-25}$ straight-chain alkenylene; and
$L^{5'}$, $L^{6'}$, $L^{7'}$, and $L^{8'}$ are each independently selected from $C_{2-25}$ straight-chain alkylene, $C_{2-25}$ straight-chain alkenylene, and $C_{2-25}$ straight-chain alkynylene.

In some embodiments, $X^4$ is a sulfonyloxy based leaving group (e.g., p-toluenesulfonyloxy, methyl sulfonyloxy, m-nitrophenyl sulfonyloxy, p-bromophenyl sulfonyloxy, or triflate), chloro, bromo, or iodo. In some embodiments, $X^4$ is bromo. In some embodiments, $X^4$ is one of the leaving groups described previously for Y.

In some embodiments, the strong base is n-butyllithium. In some embodiments, the strong base is sodium amide. In some embodiments, the strong base is one of the strong bases described previously.

In some embodiments, any of the intermediates described in the embodiments herein may be present as the free base. In some embodiments, any of the intermediates described in the embodiments herein may be present as a salt. In some embodiments, the intermediates described herein are the hydrate or solvate form.

In some embodiments, the present invention provides any of the individual process steps or intermediate compounds described supra.

Each of the processes and compounds described supra (including those in the text following Schemes 1-7) includes the following embodiments, for $R^1$, $R^{1a}$, $L^1$, $L^2$, $P^1$, $P^2$, X, Y, $L^5$, $L^6$, $L^7$, $L^8$, $L^{5'}$, $L^{6'}$, $L^{7'}$, $L^{8'}$, $L^{1'}$, $L^{2'}$, $X^1$, $X^2$, $X^3$, $X^4$, $X^5$, $X^6$, $R^a$, $R^b$, $R^c$, $R^d$, $R^e$, M, and $M^1$.

In some embodiments, $R^1$ is phenyl.

In some embodiments, each $R^{1a}$ is independently selected from halogen, cyano, nitro, hydroxyl, $C_{1-6}$ alkyl, $C_{1-6}$haloalkyl, $C_{1-6}$alkoxy, and $C_{1-6}$haloalkoxy. In some embodiments, each $R^{1a}$ is independently selected from halogen, cyano, nitro, $C_{1-6}$ alkyl, and $C_{1-6}$ alkoxy. In some embodiments, each $R^{1a}$ is independently selected from $C_{1-6}$ alkyl.

In some embodiments, $L^1$ is $C_{8-50}$ straight-chain alkylene; which is optionally substituted with 1, 2, 3, 4, 5, or 6 independently selected $R^a$ groups. In some embodiments, $L^1$ is $C_{8-50}$ straight-chain alkylene. In some embodiments, $L^1$ is selected from $C_{8-50}$ straight-chain alkylene and $C_{5-50}$ straight-chain alkenylene. In some embodiments, $L^1$ is $C_{8-50}$ straight-chain alkylene. In some embodiments, $L^1$ is $C_{8-50}$ straight-chain alkenylene.

In some embodiments, $L^2$ is selected from $C_{10-50}$ straight-chain alkylene and $C_{10-50}$ straight-chain alkenylene; which is optionally substituted with 1, 2, 3, 4, 5, or 6 independently selected $R^a$ groups. In some embodiments, $L^2$ is selected from $C_{10-50}$ straight-chain alkylene and $C_{10-50}$ straight-chain alkenylene. In some embodiments, $L^2$ is $C_{10-50}$ straight-chain alkenylene. In some embodiments, $L^2$ is $C_{10-50}$ straight-chain alkylene.

In some embodiments, the moiety $L^2$-$CH_2$-$L^1$ is at least 20 carbons in length. In some embodiments, the moiety $L^2$-$CH_2$-$L^1$ is at least 25 carbons in length. In some embodiments, the moiety $L^2$-$CH_2$-$L^1$ is from 25 carbons to 40 carbons in length. In some embodiments, the moiety $L^2$-$CH_2$-$L^1$ is saturated. In some embodiments, the moiety $L^2$-$CH_2$-$L^1$ is unsaturated (e.g., having at least one double bond). In some embodiments, the compound of Formula I is an omega-3 fatty acid. In some embodiments, the compound of Formula I is an omega-6 fatty acid. In some embodiments, $L^1$ and $L^2$ are each unbranched.

In some embodiments, $L^{1'}$ and $L^{2'}$ are each independently selected from $C_{8-40}$ straight-chain alkynylene. In some embodiments, $L^{1'}$ and $L^{2'}$ are each independently selected from $C_{10-30}$ straight-chain alkynylene. In some embodiments, $L^{1'}$ and $L^{2'}$ are each independently selected from $C_{10-20}$ straight-chain alkynylene.

In some embodiments, $L^5$, $L^6$, $L^7$, and $L^8$ are each independently selected from $C_{2-25}$ straight-chain alkylene. In some embodiments, $L^5$, $L^6$, $L^7$, and $L^8$ are each independently selected from $C_{2-25}$ straight-chain alkenylene. In some embodiments, $L^5$, $L^6$, and $L^7$ are each independently selected from $C_{2-25}$ straight-chain alkenylene. In some embodiments, $L^8$ is selected from $C_{2-25}$ straight-chain alkylene. In some embodiments, $L^5$, $L^6$, $L^7$, and $L^8$ are each independently selected from $C_{4-20}$ straight-chain alkylene. In some embodiments, $L^5$, $L^6$, $L^7$, and $L^8$ are each independently selected from $C_{4-20}$ straight-chain alkenylene. In some embodiments, $L^5$, $L^6$, and $L^7$ are each independently selected from $C_{4-20}$ straight-chain alkenylene. In some embodiments, $L^8$ is selected from $C_{4-20}$ straight-chain alkylene.

In some embodiments, $L^{5'}$, $L^{6'}$, $L^{7'}$, and $L^{8'}$ are each independently selected from $C_{2-25}$ straight-chain alkylene. In some embodiments, $L^{5'}$, $L^{6'}$, $L^{7'}$, and $L^{8'}$ are each independently selected from $C_{2-25}$ straight-chain alkenylene. In some embodiments, $L^{5'}$, $L^{6'}$, $L^{7'}$, and $L^{8'}$ are each independently selected from $C_{2-25}$ straight-chain alkynylene.

In some embodiments, $L^{5'}$, $L^{6'}$, and $L^{7'}$ are each independently selected from $C_{2-25}$ straight-chain alkylene. In some embodiments, $L^{5'}$, $L^{6'}$, and $L^{7'}$ are each independently selected from $C_{2-25}$ straight-chain alkenylene. In some embodiments, $L^{5'}$, $L^{6'}$, and $L^{7'}$ are each independently selected from $C_{2-25}$ straight-chain alkynylene. In some embodiments, $L^{5'}$, $L^{6'}$, $L^{7'}$, and $L^{8'}$ are each independently selected from $C_{4-20}$ straight-chain alkylene. In some embodiments, $L^{5'}$, $L^{6'}$, $L^{7'}$, and $L^{8'}$ are each independently selected from $C_{4-20}$ straight-chain alkenylene. In some embodiments, $L^{5'}$, $L^{6'}$, and $L^{7'}$ are each independently selected from $C_{4-20}$ straight-chain alkynylene. In some embodiments, $L^{8'}$ is selected from $C_{4-20}$ straight-chain alkylene.

In some embodiments, $P^1$ is tert-butyldimethylsilyl.

In some embodiments, Y is p-toluenesulfonyloxy, methyl sulfonyloxy, m-nitrophenyl sulfonyloxy, p-bromophenyl sulfonyloxy, triflate, chloro, bromo, or iodo. In some embodiments, Y is p-toluenesulfonyloxy. In some embodiments, Y is halogen. In some embodiments, Y is bromo.

In some embodiments, $X^1$ is p-toluenesulfonyloxy, methyl sulfonyloxy, m-nitrophenyl sulfonyloxy, p-bromophenyl sulfonyloxy, triflate, chloro, bromo, or iodo. In some embodiments, $X^1$ is halogen. In some embodiments, $X^1$ is bromo. In some embodiments, $X^1$ is p-toluenesulfonyloxy.

In some embodiments, $X^2$ is p-toluenesulfonyloxy, methyl sulfonyloxy, m-nitrophenyl sulfonyloxy, p-bromophenyl sulfonyloxy, triflate, chloro, bromo, or iodo. In some embodiments, $X^2$ is p-toluenesulfonyloxy. In some embodiments, $X^2$ is halogen. In some embodiments, $X^2$ is bromo. In some embodiments, $X^2$ is p-toluenesulfonyloxy.

In some embodiments, $X^3$ is p-toluenesulfonyloxy, methyl sulfonyloxy, m-nitrophenyl sulfonyloxy, p-bromophenyl sulfonyloxy, triflate, chloro, bromo, or iodo. In some embodiments, $X^3$ is p-toluenesulfonyloxy. In some embodiments, $X^3$ is halogen. In some embodiments, $X^3$ is bromo. In some embodiments, $X^3$ is p-toluenesulfonyloxy.

In some embodiments, $X^4$ is p-toluenesulfonyloxy, methyl sulfonyloxy, m-nitrophenyl sulfonyloxy, p-bromophenyl sulfonyloxy, triflate, chloro, bromo, or iodo. In some embodiments, $X^4$ is p-toluenesulfonyloxy. In some embodiments, $X^4$ is halogen. In some embodiments, $X^4$ is bromo. In some embodiments, $X^4$ is p-toluenesulfonyloxy.

In some embodiments, $X^5$ is p-toluenesulfonyloxy, methyl sulfonyloxy, m-nitrophenyl sulfonyloxy, p-bromophenyl sulfonyloxy, triflate, chloro, bromo, or iodo. In some embodiments, $X^5$ is p-toluenesulfonyloxy. In some embodiments, $X^5$ is halogen. In some embodiments, $X^5$ is bromo. In some embodiments, $X^5$ is p-toluenesulfonyloxy.

In some embodiments, $X^6$ is p-toluenesulfonyloxy, methyl sulfonyloxy, m-nitrophenyl sulfonyloxy, p-bromophenyl sulfonyloxy, triflate, chloro, bromo, or iodo. In some embodiments, $X^6$ is p-toluenesulfonyloxy. In some embodiments, $X^6$ is halogen. In some embodiments, $X^6$ is bromo. In some embodiments, $X^6$ is p-toluenesulfonyloxy.

In some embodiments, X is p-toluenesulfonyloxy, methyl sulfonyloxy, m-nitrophenyl sulfonyloxy, p-bromophenyl sulfonyloxy, triflate, chloro, bromo, or iodo. In some embodiments, X is p-toluenesulfonyloxy. In some embodiments, X is halogen. In some embodiments, X is bromo. In some embodiments, X is p-toluenesulfonyloxy.

In some embodiments, each $R^a$ and $R^b$ is independently selected from $C_{1-20}$ alkyl and $C_{2-20}$ alkenyl. In some embodiments, each $R^a$ and $R^b$ is independently selected from $C_{1-10}$ alkyl and $C_{2-10}$ alkenyl. In some embodiments, each $R^a$ and $R^a$ is absent.

In some embodiments, each $R^c$ and $R^d$ is independently selected from $C_{1-20}$ alkyl, $C_{2-20}$ alkenyl, or $C_{2-20}$ alkynyl. In some embodiments, each $R^a$ and $R^b$ is independently selected from $C_{1-10}$ alkyl, $C_{2-10}$ alkenyl, or $C_{2-10}$ alkynyl. In some embodiments, each $R^c$ and $R^d$ is absent.

In some embodiments, each $R^e$ is methyl.

In some embodiments, M is lithium. In some embodiments, M is sodium.

In some embodiments, $M^1$ is sodium. In some embodiments, $M^1$ is lithium.

In some embodiments, the present invention provides any of the intermediate or end products described in the embodiments herein. In some embodiments, the present invention provides any of the process step embodiments described herein.

The present invention provides a pharmaceutical composition comprising a compound of Formula I, or pharmaceutically acceptable salt thereof, and a pharmaceutically acceptable carrier.

Use of VLPUFA's in supplements may be beneficial for treating patients with macular degeneration, such as Stargardt-3 macular dystrophy (see Agbada, et al., "Role of Stargardt-3 macular dystrophy protein (ELOVL4) in the biosynthesis of very long chain fatty acids", Proceedings of the National Academy of Sciences, 105 (35):12843-12848 (2008); and McMahon, et al., "Retinal pathology and skin barrier defect in mice carrying Stargardt-3 disease-3 mutation in elongase of very long chain fatty acids-4", Molecular Vision 13:258-272 (2007), each of which is incorporated herein by reference in its entirety). Patients with mutations in the ELOVL4 gene responsible for producing the VLPUFA's in the retina may benefit from supplements. Genetic variation in the ELOVL4 gene has been found with age-related macular degeneration. The supplements may also be of value in treating retinal degenerations of hereditary and non-hereditary types, given the established role of inflammation in the conditions. Supplements may be of benefit is preventing vision loss in patients with macular degeneration. The VLPUFAs are also found in the brain, and supplement may benefit brain function. The VLPUFAs may have anti-inflammatory properties, like other PUFAs and be of value in treating inflammatory conditions.

Accordingly, the present invention further provides a method of treating macular degeneration or improving retinal development in an individual in need thereof, comprising administering a therapeutically effective amount of a compound of Formula I, or a pharmaceutically acceptable salt thereof, to said individual. In some embodiments, the macular degeneration is Stargardt-3 macular dystrophy. The present invention also provides a method of treating inflammation in an individual in need thereof, comprising administering a compound of Formula I, or pharmaceutically acceptable salt thereof, to said individual. In some embodiments, the individual is an infant. In some embodiments, the individual is a fetus. In some embodiments, the individual is a juvenile (e.g., a person under 16 years of age). In some embodiments, the compound or salt thereof, is administered to a pregnant woman in order to improve retinal development in the child. In some embodiments, the compound, or salt thereof, is administered as part of a formula to the infant after birth or as addition to breast milk.

There are a number of animal models that simulate portions of age-related macular degeneration. Theses animal models include smoke, chemical, and genetic mutations induced retinal damage models (Edwards and Malek, Angiogenesis, 2007). There are good animal models for macular dystrophies such as Best disease and retinal degenerations such as retinitis pigmentosa. The models can be used to test the role of VLPUFAs in protecting against retinal damage.

In some embodiments, certain fatty acids prepared by the processes described herein may be useful as excipients for pharmaceutical or personal care formulations.

The phrase "therapeutically effective amount" refers to the amount of a compound of the invention that elicits the biological or medicinal response in a tissue, system, animal, individual, patient, or human that is being sought by a researcher, veterinarian, medical doctor or other clinician. The desired biological or medicinal response may include preventing the disorder in an individual (e.g., preventing the disorder in an individual that may be predisposed to the disorder, but does not yet experience or display the pathology or symptomatology of the disease). The desired biological or medicinal response may also include inhibiting the disorder in an individual that is experiencing or displaying the pathology or symptomatology of the disorder (i.e., arresting or slowing further development of the pathology and/or symptomatology). The desired biological or medicinal response may also include ameliorating the disorder in an individual that is experiencing or displaying the pathology or symptomatology of the disease (i.e., reversing the pathology or symptomatology).

The therapeutically effective amount provided in the treatment of a specific disorder will vary depending the specific disorder(s) being treated, the size, age, and response pattern of the individual the severity of the disorder(s), the judgment of the attending clinician, the manner of administration, and the purpose of the administration, such as prophylaxis or therapy. In general, effective amounts for daily oral administration may be about 0.01 to 50 mg/kg, preferably about 0.1 to 10 mg/kg and effective amounts for parenteral administration may be about 0.01 to 10 mg/kg, preferably about 0.1 to 5 mg/kg.

The compounds of the invention may be administered orally or parenterally, neat or in combination with one or more conventional pharmaceutically acceptable carriers or excipients. Accordingly, the present invention provides a pharmaceutical composition which comprises a compound of Formula I, or a pharmaceutically salt thereof, and a pharmaceutically acceptable carrier. The pharmaceutical compositions can include all of the embodiments for the compounds of Formula I hereinbefore described, including various combinations and subcombinations of the embodiments.

Solid carriers suitable for use in the compositions of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided active ingredient. As used herein, the term "active ingredient" refers to a compound of Formula I, or a pharmaceutically acceptable salt thereof. In tablets, the active ingredient may be mixed with a carrier having the necessary compression properties in suitable proportions and compacted in the shape and size desired. The powders and tablets may contain up to 99% by weight of the active ingredient. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the compositions of the invention. The active ingredient may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate. Sterile liquid carriers can be used in sterile liquid form compositions for parenteral administration. The liquid carrier for pressurized compositions can be halogenated hydrocarbon or other pharmaceutically acceptable propellant.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

The compounds of the invention can be administered rectally or vaginally in the form of a conventional suppository. For administration by intranasal or intrabronchial inhalation or insufflation, the compounds of the present invention can be formulated into an aqueous or partially aqueous solution, which can then be utilized in the form of an aerosol. The compounds of the present invention can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

The pharmaceutical composition can be administered in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is an topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the liquid composition further comprises a polymer. These polymers may be used to improve the bioavailability, raise viscosity, or reduce drainage from the eye for a liquid formulation. In some embodiments, the polymers include, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the polymer is sodium hyaluronase, chitosan, a cyclodextrin (e.g., hydroxypropyl β-cyclodextrin), polygalactoronic acid, xyloglucan, xanthan gum, gellan gum, a thiomer, a poly(ortho ester) (e.g., as described in Einmahl, *Adv. Drug. Deliv. Rev.* 53:45-73 (2001), which is incorporated herein by reference in its entirety), or a tamarind seed polysaccharide (e.g., as described in Ghelardi, et al., Antimicrob. Agents Chemother. 48:3396-3401 (2004), which is incorporated herein by reference in its entirety).

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the osmotic pressure of the ophthalmic composition may be from about 10 milliosmolar (mOsM) to about 400 mOsM, or from 260 to about 340 mOsM. In some embodiments, the osmotic pressure can be adjusted by using appropriate amounts of physiologically and ophthalmically acceptable salts or excipients. In further embodiments, sodium chloride may be used to approximate physiologic fluid. In other embodiments, the composition comprises sodium chloride ranging from about 0.01% to about 1% by weight, or from about 0.05% to about 0.45% by weight, based on the total weight of the composition. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above stated range. Similarly, a sugar such as mannitol, dextrose, sorbitol, glucose and the like can also be used to adjust osmolality.

In some embodiments, the methods involve forming or supplying a depot of the compound or salt in contact with the external surface of the eye. A depot refers to a source of therapeutic agent that is not rapidly removed by tears or other eye clearance mechanisms. This allows for continued, sustained high concentrations of therapeutic agent be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, a semi-solid composition is a liquid formulation which increases in viscosity upon application to the eye, usually because of a polymer in the liquid formulation. This viscosity increase may be triggered by a change in temperature, pH, or electrolyte concentration. In some embodiments, the polymer include, but are not limited to, those described for semi-solid dosage forms in Wagh, et al., "Polymers used in ocular dosage form and drug delivery systems", *Asian J. Pharm.*, pages 12-17 (January 2008), which is incorporated herein by reference in its entirety. In some embodiments, the polymer is celluloseacetophthalate, polyacrylic acid, gellan gum, hyaluronase, chitosan, salts of alginic acid (e.g., sodium alginate), or a block copolymer of ethylene oxide and propylene oxide (e.g., Pluronic®, BASF; poloxamer). In some embodiments, the polyacrylic acid is crosslinked acrylic acid (e.g., Carbopol®). In some embodiments, the semi-solid composition comprises a mixture of carbopol and a block copolymer of ethylene oxide and propylene oxide; a mixture of methyl cellulose and hydroxyethyl cellulose; or a mixture of polyethylene glycol and a block copolymer of ethylene oxide and propylene oxide.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly(dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al., "Polymers used in ocular dosage form and drug delivery systems", *Asian J. Pharm.*, pages 12-17 (January 2008), In some embodiments, the film is a soft-contract lense, such as ones made from copolymers of N,N-diethylacrylamide and methacrylic acid crosslinked with ethyleneglycol dimethacrylate.

In some embodiments, the insert comprises a core comprising the therapeutic agent and an outer tube (see e.g., U.S. Patent Pub. No. 20040009222, which is incorporated herein by reference in its entirety). In some embodiments, the outer tube may be permeable, semi-permeable, or impermeable to the drug. In some embodiments, the drug core may include a polymer matrix which does not significantly affect the release rate of the drug. In some embodiments, the outer tube, the polymer matrix of the drug core, or both may be bioerodible. In some embodiments, the co-extruded product can be segmented into drug delivery devices. In some embodiments, the devices may be left uncoated so that their respective ends are open, or the devices may be coated with, for example, a layer that is permeable to the therapeutic agent, semi-permeable to the therapeutic agent, or bioerodible. In certain embodiments, the therapeutic agent and at least one polymer are admixed in powder form. In some embodiments, the insert is formed by forwarding a polymeric material to a first extrusion device, forwarding an therapeutic agent to a second extrusion device, co-extruding a mass including the polymeric material and the therapeutic agent, and forming the mass into at least one co-extruded drug delivery device which comprises a core including the therapeutic agent and an outer layer including the polymeric material. In certain embodiments, the therapeutic agent forwarded to the second extrusion device is in admixture with at least one polymer. In certain embodiments, the therapeutic agent and at least one polymer are admixed in powder form. In certain embodiments, this act includes forwarding more than one drug to the second extrusion device. In certain embodiments, the polymeric material is one of impermeable, semi-permeable, or permeable to the therapeutic agent. The polymeric material may be bioerodible and/or radiation curable. In latter instances, the insert may be irradiated.

In certain embodiments, the insert is in a tubular form, and may be segmented into a plurality of shorter products. In certain embodiments, the insert further comprises a coating of the plurality of shorter products with one or more layers including at least one of a layer that is permeable to the therapeutic agent, a layer that is semi-permeable to the therapeutic agent, and a layer that is bioerodible. The polymeric material may include any biocompatible polymer, such as polycaprolactone (PCL), an ethylene/vinyl acetate copolymer (EVA), polyalkyl cyanoacrylate, polyurethane, a nylon, or poly(dl-lactide-co-glycolide) (PLGA), or a copolymer of any of these.

In some embodiments, the insert comprises a therapeutically effective amount of at least one therapeutic agent coated by or dispersed in a polymer matrix, wherein the therapeutic agent is in granular or particulate form. In some embodiments, the therapeutic agent is released from the formulation as drug from the granules dissolves into or within the matrix, diffuses through the matrix, and is released into the surrounding physiological fluid. In some embodiments, the rate of release is limited primarily by the rate of dissolution of the therapeutic agent from the granules/particles into the matrix; the steps of diffusion through the matrix and dispersion into the surrounding fluid are primarily not release-rate-limiting. In certain embodiments, the polymer matrix is non-bioerodible, while in other embodiments it is bioerodible. Exemplary non-bioerodible polymer matrices can be formed from polyurethane, polysilicone, poly(ethylene-co-vinyl acetate) (EVA), polyvinyl alcohol, and derivatives and copolymers thereof. Exemplary bioerodible polymer matrices can be formed from polyanhydride, polylactic acid, polyglycolic acid, polyorthoester, polyalkylcyanoacrylate, and derivatives and copolymers thereof.

In some embodiments, the insert comprises a collagenous material. In some embodiments, the insert may be a soluble ophthalmic drug insert (SODI, e.g., a polymeric oval film that can be introduced in the upper conjuctival sac for drug delivery; an elliptical insert such as OCUSERT® (Pilocarpine ocular therapeutic system, developed by Alza Corporation) which is made of ethylene vinyl acetate; OCUFIT® (developed by Escalon Ophthalmics Inc., Skillman, NS), which is a rod shaped silicone elastomer; Lacrisert®, a rod shaped insert made of cellulose; New Ophthalmic Drug Delivery Systems (NODS), made of poly(vinyl alcohol); and the inserts described in Fabrizio, *Advanced Drug Delivery Reviews* 16: 95-106, 1998, which is incorporated herein by reference in its entirety. In further embodiments, the insert can be placed, depending on the location and the mechanism used to hold the insert in position, by either the patient or the doctor. In further embodiments, the insert comprises collagen, gelatin, or a polymer, wherein the polymer is selected from polycaprolactone (PCL), an ethylene/vinyl acetate copolymer (EVA), polyalkyl cyanoacralate, polyurethane, a nylon, poly(dl-lactide-co-glycolide) (PLGA), or a copolymer of any of the aforementioned. In some embodiments, the insert is implanted under the upper eyelid. In some embodiments, the insert is implanted in the posterior segment of the eye, in the chroidal space, or in the sclera. In some embodiments, the insert is implanted intravitreally or sub-retinally. In some embodiments, the insert is injected sub-retinally. Methods of administration and techniques for their preparation are set forth in Remington's Pharmaceutical Sciences, which is incorporated herein by reference in it entirety.

In other embodiments, the insert provides a sustained release of the therapeutic agent to the vitreous of the eye. As used herein, "sustained release" means that the composition releases the therapeutic agent over an extended period of time in a controlled fashion. In some embodiments, the insert releases the therapeutic agent at a rate such that the aqueous therapeutic agent concentration remains less than the vitreous therapeutic agent concentration during the release. In some embodiments, the aqueous therapeutic agent concentration is from about 0.002 µg/mL to about 0.01 µg/mL, or from about 0.01 µg/mL to about 0.05 µg/mL, or less than about 0.05 µg/mL. In some embodiments, the therapeutic agent is released at a rate of about 1 µg/day to about 50 µg/day, or from about 1 µg/day to about 10 µg/day. In some embodiments, the insert further comprises an additional therapeutic agent, as detailed above, e.g., fluocinolone acetonide (such as that found in the ophthalmic insert Retisert®).

In some embodiments, the ophthalmic composition comprises microspheres or nanoparticles. In some embodiment, the microspheres comprise gelatin. In some embodiments, the microspheres are injected to the posterior segment of the eye, in the chroidal space, in the sclera, intravitreally or sub-retinally. In some embodiments, the microspheres or nanoparticles comprises a polymer including, but not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl) caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium (e.g., having the properties as described above). In some embodiment, the therapeutic agent is suspended. In some embodiments, the therapeutic agent is in solution. In further embodiments, the suspending agent serves to provide stability to the suspension, to increase the residence time of the dosage form on the eye, or to enhance the sustained release of the drug in terms of both longer release times and a more uniform release curve. Examples of polymeric suspending agents include, but are not limited to, dextrans, polyethylene glycols, polyvinylpyrolidone, polysaccharide gels, Gelrite®, cellulosic polymers like hydroxypropyl methylcellulose, and carboxy-containing polymers such as polymers or copolymers of acrylic acid, as well as other polymeric demulcents. In some embodiments, the polymeric suspending agent is a water swellable, water insoluble polymer, especially a crosslinked carboxy-containing polymer. In some embodiments, the polymeric suspending agent comprises from at least about 90% to about 99.9%, or from about 95% to about 99.9%, by weight based on the total weight of monomers present, of one or more carboxy-containing monoethylenically unsaturated monomers. In some embodiments, the carboxy-containing monoethylenically unsaturated monomer includes acrylic acid, methacrylic acid, ethacrylic acid, methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, phenylacrylic acid (cinnamic acid), coumaric acid (o-hydroxycinnamic acid), and umbellic acid (p-hydroxycoumaric acid). In some embodiments, the polymers may be crosslinked by a polyfunctional crosslinking agent (e.g., a difunctional crosslinking agent). In further embodiments, the amount of crosslinking should be sufficient to form insoluble polymer particles, but not so great as to unduly interfere with sustained release of the therapeutic agent. In some embodiment, the polymers are only lightly crosslinked. In some embodiments, the crosslinking agent is contained in an amount of from about 0.01% to about 5%, or from about 0.1% to about 5.0%, or from about 0.2% to about 1%, based on the total weight of monomers present. In some embodiments, the crosslinking agents are nonpolyalkenyl polyether difunctional crosslinking monomers such as divinyl glycol, 2,3-dihydroxyhexa-1,5-diene, 2,5-dimethyl-1,5-hexadiene, divinylbenzene, N,N-diallylacrylamide, N,N-diallymethacrylamide; polyalkenyl polyether crosslinking agents containing two or more alkenyl ether groupings per molecule, e.g., alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; diolefinic non-hydrophilic macromeric crosslinking agents having molecular weights of from about 400 to about 8,000, such as insoluble diacrylates and polyacrylates and methacrylates of diols and polyols, diisocyanate hydroxyalkyl acrylate or methacrylate reaction products of isocyanate terminated prepolymers derived from polyester diols, polyether diols or polysiloxane diols with hydroxyalkylmethacrylates, and the like.

In some embodiments, the crosslinked polymers may be made from a carboxy-containing monoethylenically unsaturated monomer or monomers as the sole monoethylenically unsaturated monomer present, together with a crosslinking agent or agents. In some embodiments, the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrrolidone, and the like (see Mueller et al. U.S. Pat. No. 4,548,990, the entire contents of which are incorporated herein by reference, for a more extensive listing of such additional monoethylenically unsaturated monomers). In some embodiments, the polymers include polycarbophil (Noveon AA-1), Carbopol®, and DuraSite®. In some embodiments, the crosslinked polymers are prepared by suspension or emulsion polymerizing the monomers, using conventional free radical polymerization catalysts, to a dry particle size of not more than about 50 μm in equivalent spherical diameter. In some embodiments, the average dry particle size is from about 1 to about 30 μm, or from about 3 to about 20 μm in equivalent spherical diameter. In some embodiments, the polymer particles are obtained by mechanically milling larger polymer particles. In further embodiments, such polymers will have a molecular weight from about 250,000 to about 4,000,000, and from 3,000,000,000 to 4,000,000,000. In other embodiments, the particles of crosslinked polymer are monodisperse, meaning that they have a particle size distribution such that at least about 80%, about 90% or about 95%, of the particles fall within a μm band of major particle size distribution. In further embodiments, the monodisperse particle size means that there is no more than about 20%, about 10%, or about 5% particles of a size below 1 μm. In some embodiments, the aqueous polymeric suspension comprises from about 0.05 to about 1%, from about 0.1 to about 0.5%, or from about 0.1 to about 0.5%, of the therapeutic agent and from about 0.1 to about 10%, from about 0.5 to about 6.5%, from about 0.5 to about 2.0%, from about 0.5% to about 1.2%, from about 0.6 to about 0.9%, or from about 0.6 to about 0.8% of a polymeric suspending agent. Although referred to in the singular, it should be understood that one or more species of polymeric suspending agent can be used with the total amount falling within the stated ranges. In one embodiment, the amount of insoluble lightly crosslinked polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm. In some embodiments, the viscosity is from about 10 to about 400 centipoise, from about 10 to about 200 centipoises or from about 10 to about 25 centipoise.

In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid. For instance, when a formulation containing DuraSite® or other similar polyacrylic acid-type polymer is administered to the eye at a pH of less than about 6.7, the polymer may swell upon contact with tear fluid since it has a higher pH (around 7). This gelation or increase in gelation may lead to entrapment of the suspended particles, thereby extending the residence time of the composition in the eye. In some embodiments, the therapeutic agent is released slowly as the suspended particles dissolve over time. In some embodiments, this delivery route increases patient comfort and increased therapeutic agent contact time with the eye tissues, thereby increasing the extent of drug absorption and duration of action of the formulation in the eye. The therapeutic agents contained in these drug delivery systems may be released from the gels at rates that depend on such factors as the drug itself and its physical form, the extent of drug loading and the pH of the system, as well as on any drug delivery adjuvants, such as ion exchange resins compatible with the ocular surface, which may also be present.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. In some embodiments, the compounds of Formula I can be synthesized as in the Scheme 8 below:

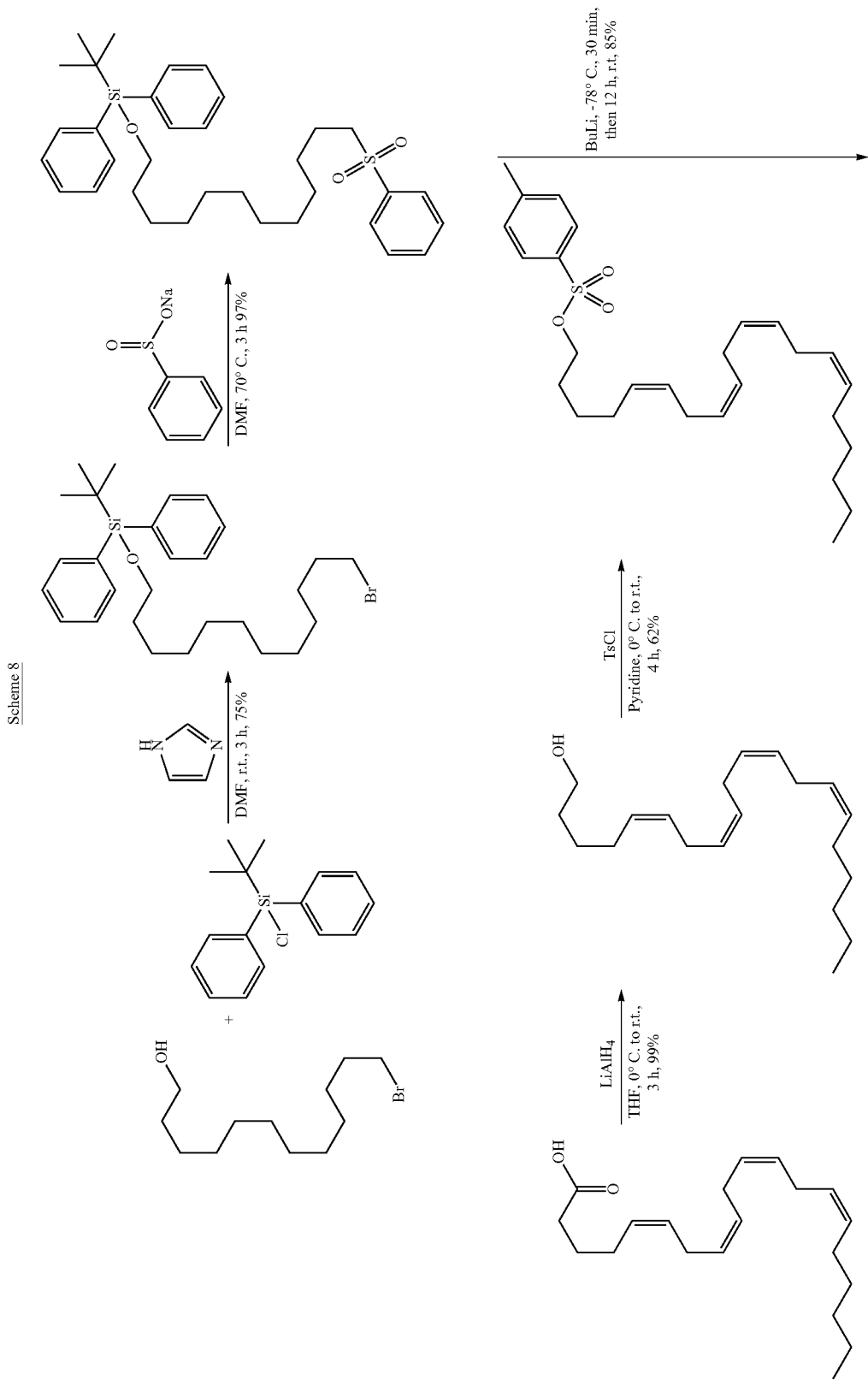

-continued
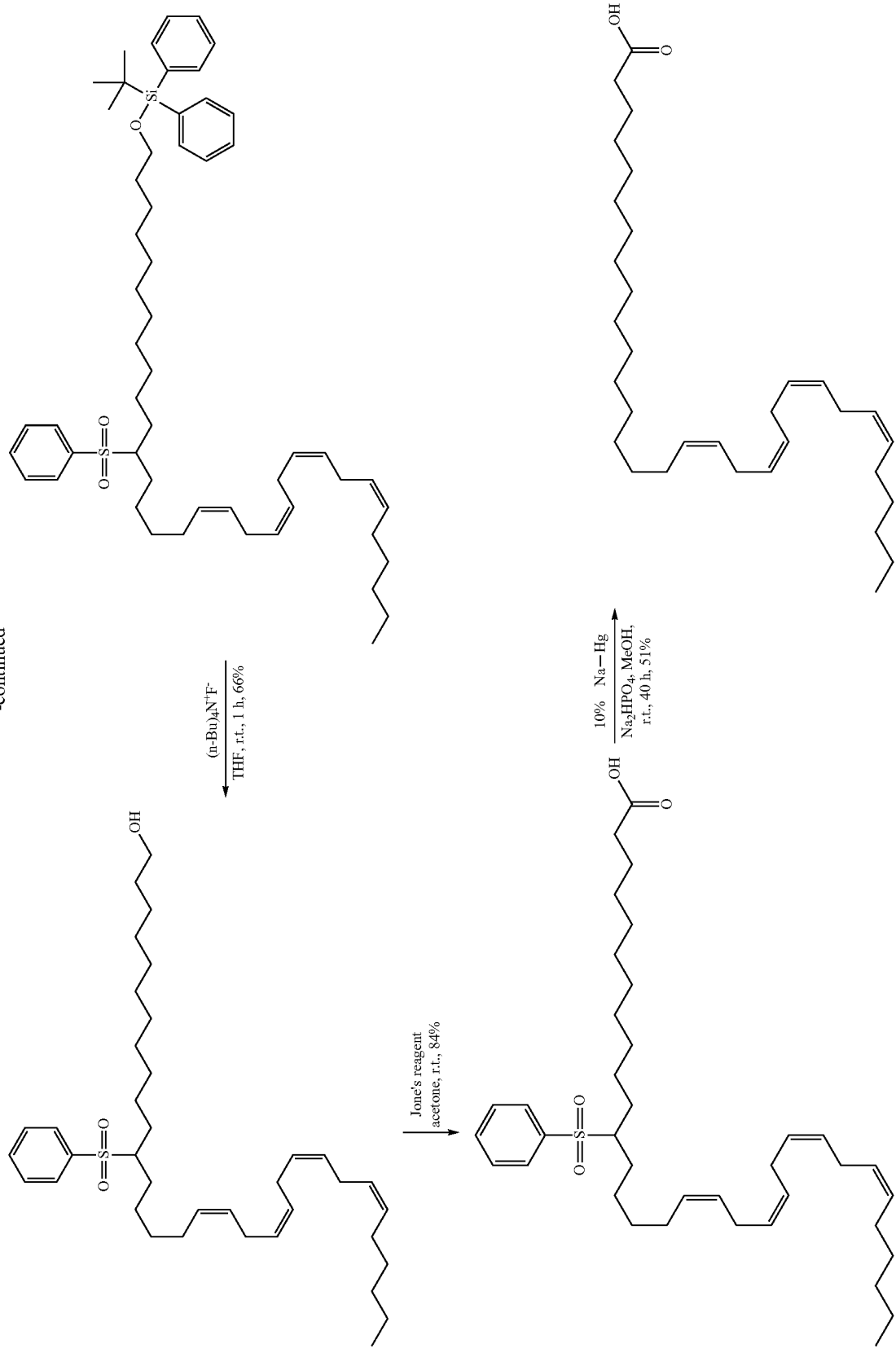

Example 1

(12-Bromododecyloxy)(tert-butyl)diphenylsilane

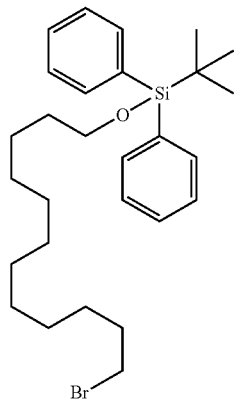 [SMILES: CC(C)(C)[Si](OCCCCCCCCCCCCBr)(c1ccccc1)c1ccccc1]

1-Bromododecanol (2.511 g, 9.47 mmol), tert-butyldiphenylsilylchloride (2.66 mL, 15.15 mmol), and imidazole (1.418 g, 20.83 mmol) were dissolved in dry DMF (20 mL) and the resulting mixture was stirred under nitrogen for 3 h at room temperature. Upon completion of reaction, water (15 mL) and diethyl ether (25 mL) were added, the two layers were separated and the water layer was extracted with diethyl ether (3×25 mL). The combined organic extracts were washed with water, brine, dried over MgSO$_4$, filtered and filtrate evaporated. The crude was purified by silica gel column chromatography using 100% hexane to 5% ethyl acetate/hexane as eluent to afford the title product as a clear thick oil (3.57 g, 75%). $^1$H NMR (CDCl$_3$): δ7.66 (m, 4H), 7.39 (m, 6H), 3.62 (t, 2H, J=6.5 Hz), 3.40 (t, 2H, J=6.9 Hz), 1.85 (m, 2H), 1.54 (m, 2H), 1.44-1.25 (m, 16H), 1.04 (s, 9H). m/z (APCI) 505.37 (M$^+$+1).

Example 2 tert-Butyldiphenyl(12-(phenylsulfonyl)dodecyloxy)silane

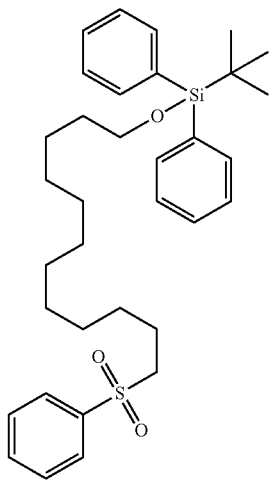 [SMILES: CC(C)(C)[Si](OCCCCCCCCCCCCS(=O)(=O)c1ccccc1)(c1ccccc1)c1ccccc1]

(12-Bromododecyloxy)(tert-butyl)diphenylsilane (8.535 g, 16.95 mmol), and sodium sulfinate 11.13 g, 67.80 mmol) were dissolved in dry DMF (50 mL) and stirred at 70° C. under nitrogen for 3 h. Upon completion of reaction, water (30 mL) and diethyl ether (50 mL) were added, the two layers were separated and the water layer was extracted with diethyl ether (3×50 mL). The combined organic extracts were washed with water, brine, dried over MgSO$_4$, filtered and evaporated under reduced pressure. The crude was purified by silica gel column chromatography using 10% ethyl acetate/hexane as eluent to afford the title product as a clear thick oil (9.29 g, 97.0%). $^1$H NMR (CDCl$_3$): δ7.91 (d, 2H, J=7.22 Hz), 7.66 (m, 3H), 7.56 (m, 4H), 7.39 (m, 6H), 3.64 (t, 2H, J=6.5 Hz), 3.07 (t, 2H, J=6.8 Hz), 1.87 (m, 2H), 1.58 (m, 2H), 1.44-1.25 (m, 16H), 1.04 (s, 9H). m/z (APCI) 487.43 (M$^+$+Na).

Example 3

(5Z,8Z,11Z,14Z)-Icosa-5,8,11,14-tetraen-1-ol

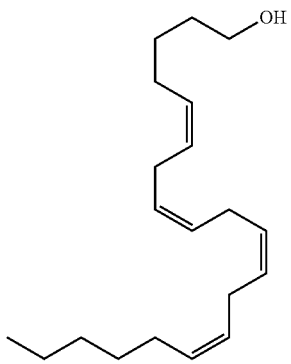 [SMILES: CCCCC/C=C\C/C=C\C/C=C\C/C=C\CCCCO]

To a suspension of LiAlH$_4$ (0.499 g, 13.14 mmol) in dry THF (50 mL) was added arachidonic acid (1.00 g, 3.28 g) in dry THF (40 mL) at 0° C. (ice-bath) under argon and the reaction mixture was stirred for 1 h at 0° C. and then for 1 h at room temperature. After a slow addition of water (0.2 mL), the white gelatinious precipitate was dissolved by adding 10% aq NaOH (0.2 mL) and water (0.6 mL) and the mixture was allowed to stir for 1 h. The mixture was then dried over MgSO$_4$, and filtered and the filtrate was concentrated under reduced pressure to furnish a crude, which was purified over silica-gel column chromatography using 20% ethyl acetate/hexane to give the product as a clear oil (0.945 g, 99%). $^1$H NMR (CDCl$_3$): δ5.37 (m, 8H), 3.64 (t, 2H, J=6.4 Hz), 2.81 (m, 6H), 2.09 (m, 4H), 1.61 (m, 2H), 1.50-1.30 (m, 8H), 1.04 (t, 3H, J=6.8 Hz). m/z (APCI) 291.43 (M$^+$+1).

Example 4

(5Z,8Z,11Z,14Z)-Icosa-5,8,11,14-tetraenyl-4-methylbenzenesulfonate

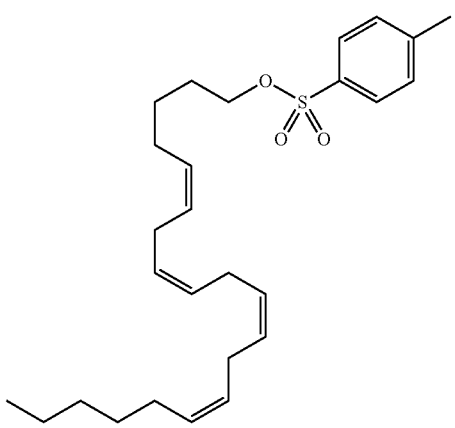 [SMILES: CCCCC/C=C\C/C=C\C/C=C\C/C=C\CCCCOS(=O)(=O)c1ccc(C)cc1]

(5Z,8Z,11Z,14Z)-Icosa-5,8,11,14-tetraen-1-ol (0.58 g, 1.997 mmol) was dissolved in pyridine (8 mL) and to this solution p-toluenesulfonyl chloride (0.762 g, 3.99 mmol) was added at 0° C. (ice-bath) and the reaction mixture was stirred under nitrogen for 4 h as the temperature was slowly allowed to rise to room temperature. The solvent was then removed under reduced pressure and the crude was purified on silica gel column chromatography using 5%-10% ethyl/hexane giving the title product as a clear oil (0.551 g, 62%). $^1$H NMR (CDCl$_3$): δ 7.79 (d, 2H, J=8.2 Hz), δ 7.34 (d, 2H, J=8.2 Hz), 5.35 (m, 8H), 4.02 (t, 2H, J=6.4 Hz), 2.79 (m, 6H), 2.44 (s, 3H), 2.03 (m, 4H), 1.64 (m, 2H), 1.43-1.25 (m, 8H), 1.04 (t, 3H, J=6.8 Hz). m/z (ESI) 467.27 (M$^+$+Na).

Example 5 tert-Butyldiphenyl((17Z,20Z,23Z,26Z)-12-(phenyl-sulfonyl)dotriaconta-17,20,23,26-tetraenyloxy)silane Example 6

(17Z,20Z,23Z,26Z)-12-(Phenylsulfonyl)dotriaconta-17,20,23,26-tetraen-1-ol

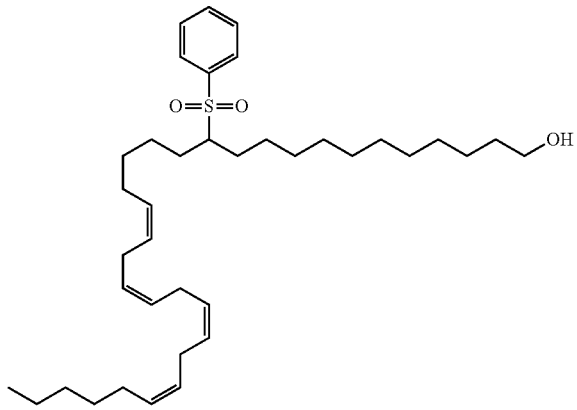

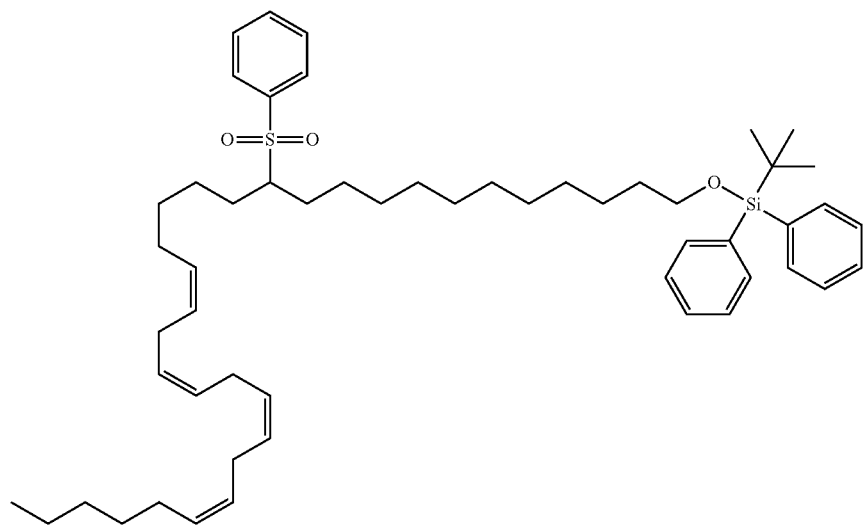 [SMILES: CCCCC/C=C\C/C=C\C/C=C\C/C=C\CCCCC(CCCCCCCCCCCO[Si](c1ccccc1)(c1ccccc1)C(C)(C)C)S(=O)(=O)c1ccccc1]

To a stirred solution of tert-butyldiphenyl(12-(phenylsulfonyl)dodecyloxy)silane (0.381 g, 0.675 mmol) in THF (2 mL) was added n-BuLi (2.5 M solution in hexanes, 0.297 mL, 0.742 mmol) at −78° C. under Argon. After stirring the resulting solution for 30 min, the reaction mixture was slowly warmed to room temperature and stirred overnight. The reaction mixture was quenched with saturated aqueous NH$_4$Cl (2 mL) at −10° C. and the aqueous phase was extracted with DCM (3×15 mL). The combined organic extracts were washed with brine, dried over MgSO$_4$, filtered and concentrated. The crude was purified by silica gel column chromatography using 5% ethyl acetate/hexane to afford the title product as a clear thick oil (0.16 g, 85%). $^1$H NMR (CDCl$_3$): δ7.89-7.39 (m, 15H), 5.37 (m, 8H), 3.64 (t, 2H, J=6.5 Hz), 2.78 (m, 7H), 2.08 (m, 4H), 1.82 (m, 2H), 1.37-1.20 (m, 30H), 1.04 (s, 9H), 1.04 (t, 3H, J=6.7 Hz). m/z (ESI) 837.74 (M$^+$+1).

Tetrabutylammonium fluoride (1 M solution in THF, 0.764 mL, 0.764 mmol) was added drop wise to a stirred solution of tert-butyldiphenyl((17Z,20Z,23Z,26Z)-12-(phenylsulfonyl)dotriaconta-17,20,23,26-tetra-enyloxy)silane (0.16 g, 0.191 mmol) in dry THF (2 mL) and stirring was continued for 1 h. Upon completion of reaction as judged y TLC, water (3 mL) was added and the reaction mixture was extracted with ethyl acetate (3×15 mL). The combined organic extracts were washed with brine, dried over MgSO$_4$, filtered and concentrated. The crude was purified by silica gel column chromatography using 30% ethyl acetate/hexane to afford the title product as a clear oil (0.075 g, 66%). $^1$H NMR (CDCl$_3$): δ7.88 (d, 2H, J=7.2 Hz), 7.57 (m, 3H), 5.38 (m, 8H), 3.65 (br s, 2H), 2.81 (m, 7H), 2.05 (m, 4H), 1.81 (m, 2H), 1.37-1.20 (m, 30H), 1.04 (t, 3H, J=6.9 Hz). m/z (APCI) 599.45 (M$^+$+1).

Example 7

(17Z,20Z,23Z,26Z)-12-(phenylsulfonyl)dotriaconta-17,20,23,26-tetraenoic acid

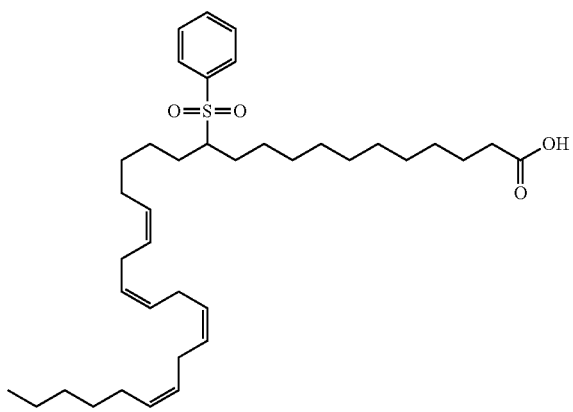 [SMILES: CCCCC/C=C\C/C=C\C/C=C\C/C=C\CCCCC(CCCCCCCCCCC(=O)O)S(=O)(=O)c1ccccc1]

Jone's reagent was added dropwise to a stirred solution of 17Z,20Z,23Z,26Z)-12-(phenylsulfonyl)dotriaconta-17,20,23,26-tetraen-1-ol (1 M solution in THF, 0.764 mL, 0.764 mmol) dissolved in acetone (5 mL) till the completion of reaction (TLC monitoring). The reaction was quenched with methanol (2 mL) and stirred for 30 min. The solvent was then removed and the crude was purified by silica gel column chromatography using 30% ethyl acetate/hexane to furnish the title compound as a clear oil (0.0643, 84%). $^1$H NMR (CDCl$_3$): δ 7.88 (d, 2H, J=7.2 Hz), 7.60 (m, 3H), 5.36 (m, 8H), 2.79 (m, 7H), 2.27 (t, 2H, J=6.8 Hz), 2.07 (m, 4H), 1.68 (m, 2H), 1.37-1.20 (m, 28H), 1.04 (t, 3H, J=6.8 Hz). m/z (APCI) 613.45 (M$^+$+1).

Example 8

(17Z,20Z,23Z,26Z)-dotriaconta-17,20,23,26-tetraenoic acid

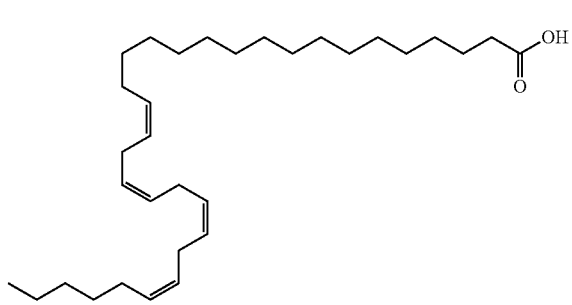 [SMILES: CCCCC/C=C\C/C=C\C/C=C\C/C=C\CCCCCCCCCCCCCCCC(=O)O]

To a solution of (17Z,20Z,23Z,26Z)-12-(phenylsulfonyl)dotriaconta-17,20,23,26-tetraenoic acid (0.0643 g, 0.105 mmol) in methanol (8 mL) was added Na$_2$HPO$_4$ (0.074 g, 0.525 mmol) and 10% sodium amalgam (5.16 g, 2.308 mmol) and the resulting reaction mixture was stirred under nitrogen at room temperature for 40 h. The solvent was decanted and acidified (pH 4) with 1M HCl. The aqueous phase was extracted with DCM (3×10 mL), washed with brine (2×10 mL), dried over MgSO$_4$, filtered and evaporated. The product from the crude was isolated by flash chromatography using 25% ethyl acetate/hexane as eluent to afford the title product as a light yellow oil (0.025 g, 51%). $^1$H NMR (CDCl$_3$): δ 5.36 (m, 8H), 2.79 (m, 6H), 2.28 (t, 2H, J=6.7 Hz), 1.99 (m, 4H), 1.61 (m, 2H), 1.51-1.18 (m, 30H), 0.97 (t, 3H, J=6.8 Hz). m/z (APCI) 473.62 (M$^+$+1).

A number of embodiments of the invention have been described. Nevertheless, it will be understood that various modifications may be made without departing from the spirit and scope of the invention.

What is claimed is:

1. A compound of Formula II:

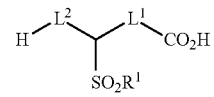

or salt thereof; wherein:
- L$^1$ is selected from C$_{4-50}$ straight-chain alkylene and C$_{4-50}$ straight-chain alkenylene; each of which is optionally substituted with 1, 2, 3, 4, 5, or 6 independently selected R$^a$ groups;
- L$^2$ is selected from C$_{4-50}$ straight-chain alkylene and C$_{4-50}$ straight-chain alkenylene; each of which is optionally substituted with 1, 2, 3, 4, 5, or 6 independently selected R$^b$ groups;
- R$^1$ is phenyl, which is optionally substituted by 1, 2, 3, 4, or 5 independently selected R$^{1a}$ groups;
- each R$^{1a}$ is independently selected from halogen, cyano, nitro, hydroxyl, C$_{1-6}$ alkyl, C$_{1-6}$ haloalkyl, C$_{1-6}$ alkoxy, C$_{1-6}$ haloalkoxy, di(C$_{1-6}$ alkyl)amino, carbamyl, C$_{1-6}$ alkylcarbamyl, di(C$_{1-6}$)alkylcarbamyl, C$_{1-6}$ alkoxycarbonyl, and C$_{1-6}$ alkylsulfonyl; and
- each R$^a$ and R$^b$ is independently selected from C$_{1-30}$ alkyl and C$_{2-30}$ alkenyl.

2. A compound according to claim 1 or salt thereof, wherein R$^1$ is phenyl.

3. A compound of Formula II:

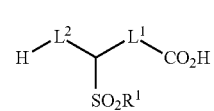

or salt thereof; wherein:
- L$^1$ is C$_{8-50}$ straight-chain alkylene; which is optionally substituted with 1, 2, 3, 4, 5, or 6 independently selected R$^a$ groups;
- L$^2$ is selected from C$_{4-50}$ straight-chain alkylene and C$_{4-50}$ straight-chain alkenylene; each of which is optionally substituted with 1, 2, 3, 4, 5, or 6 independently selected R$^b$ groups;
- R$^1$ is phenyl, which is optionally substituted by 1, 2, 3, 4, or 5 independently selected R$^{1a}$ groups;
- each R$^{1a}$ is independently selected from halogen, cyano, nitro, hydroxyl, C$_{1-6}$ alkyl, C$_{1-6}$ haloalkyl, C$_{1-6}$ alkoxy, C$_{1-6}$ haloalkoxy, di(C$_{1-6}$ alkyl)amino, carbamyl, C$_{1-6}$ alkylcarbamyl, di(C$_{1-6}$)alkylcarbamyl, C$_{1-6}$ alkoxycarbonyl, and C$_{1-6}$ alkylsulfonyl; and
- each R$^a$ and R$^b$ is independently selected from C$_{1-30}$ alkyl and C$_{2-30}$ alkenyl.

4. A compound of Formula II:

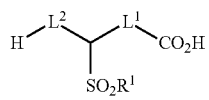

or salt thereof; wherein:
- $L^1$ is $C_{8-50}$ straight-chain alkylene;
- $L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;
- $R^1$ is phenyl, which is optionally substituted by 1, 2, 3, 4, or 5 independently selected $R^{1a}$ groups;
- each $R^{1a}$ is independently selected from halogen, cyano, nitro, hydroxyl, $C_{1-6}$ alkyl, $C_{1-6}$ haloalkyl, $C_{1-6}$ alkoxy, $C_{1-6}$ haloalkoxy, di($C_{1-6}$ alkyl)amino, carbamyl, $C_{1-6}$ alkylcarbamyl, di($C_{1-6}$)alkylcarbamyl, $C_{1-6}$ alkoxycarbonyl, and $C_{1-6}$ alkylsulfonyl; and
- each $R^b$ is independently selected from $C_{1-30}$ alkyl and $C_{2-30}$ alkenyl.

5. A compound of Formula II:

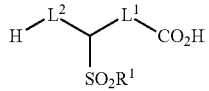

or salt thereof; wherein:
- $L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
- $L^2$ is selected from $C_{10-50}$ straight-chain alkylene and $C_{10-50}$ straight-chain alkenylene; which is optionally substituted with 1, 2, 3, 4, 5, or 6 independently selected $R^b$ groups;
- $R^1$ is phenyl, which is optionally substituted by 1, 2, 3, 4, or 5 independently selected $R^{1a}$ groups;
- each $R^{1a}$ is independently selected from halogen, cyano, nitro, hydroxyl, $C_{1-6}$ alkyl, $C_{1-6}$ haloalkyl, $C_{1-6}$ alkoxy, $C_{1-6}$ haloalkoxy, di($C_{1-6}$ alkylamino, carbamyl, $C_{1-6}$ alkylcarbamyl, di($C_{1-6}$)alkylcarbamyl, $C_{1-6}$ alkoxycarbonyl, and $C_{1-6}$ alkylsulfonyl; and
- each $R^a$ and $R^b$ is independently selected from $C_{1-30}$ alkyl and $C_{2-30}$ alkenyl.

6. A compound of Formula II:

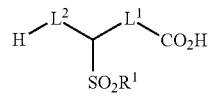

or salt thereof; wherein:
- $L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
- $L^2$ is selected from $C_{10-50}$ straight-chain alkylene and $C_{10-50}$ straight-chain alkenylene;
- $R^1$ is phenyl, which is optionally substituted by 1, 2, 3, 4, or 5 independently selected $R^{1a}$ groups;
- each $R^{1a}$ is independently selected from halogen, cyano, nitro, hydroxyl, $C_{1-6}$ alkyl, $C_{1-6}$ haloalkyl, $C_{1-6}$ alkoxy, $C_{1-6}$ haloalkoxy, di($C_{1-6}$ alkyl)amino, carbamyl, $C_{1-6}$ alkylcarbamyl, di($C_{1-6}$)alkylcarbamyl, $C_{1-6}$ alkoxycarbonyl, and $C_{1-6}$ alkylsulfonyl; and
- each $R^a$ is independently selected from $C_{1-30}$ alkyl and $C_{2-30}$ alkenyl.

7. A compound according to claim 6, or salt thereof, wherein $L^2$ is $C_{10-50}$ straight-chain alkenylene.

8. A compound of Formula II:

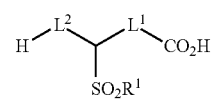

or salt thereof; wherein:
- $L^1$ is selected from $C_{4-50}$ straight-chain alkylene and $C_{4-50}$ straight-chain alkenylene; each of which is optionally substituted with 1, 2, 3, 4, 5, or 6 independently selected $R^a$ groups;
- $L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups;
- $R^1$ is phenyl, which is optionally substituted by 1, 2, 3, 4, or 5 independently selected $R^{1a}$ groups;
- each $R^{1a}$ is independently selected from halogen, cyano, nitro, hydroxyl, $C_{1-6}$ alkyl, $C_{1-6}$ haloalkyl, $C_{1-6}$ alkoxy, $C_{1-6}$ haloalkoxy, di($C_{1-6}$ alkyl)amino, carbamyl, $C_{1-6}$ alkylcarbamyl, di($C_{1-6}$)alkylcarbamyl, $C_{1-6}$ alkoxycarbonyl, and $C_{1-6}$ alkylsulfonyl; and
- each $R^a$ and $R^b$ is independently selected from $C_{1-30}$ alkyl and $C_{2-30}$ alkenyl; wherein the moiety $L^2$-$CH_2$-$L^1$ is at least 20 carbons in length.

9. A compound according to claim 1, or salt thereof, wherein the moiety $L^2$-$CH_2$-$L^1$ is at least 25 carbons in length.

10. A process of preparing a compound of Formula I:

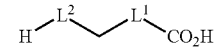

or salt thereof; comprising desulfonating a compound of formula II according to claim 1, or salt thereof, to form a compound of Formula I.

11. The process according to claim 10, wherein the desulfonating comprises treating with sodium-mercury amalgam.

12. The process according to claim 10, further comprising preparing the compound of Formula II:

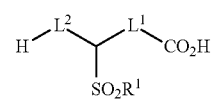

or salt thereof, by a process comprising oxidizing a compound of Formula III:

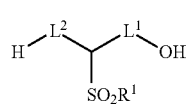

III or salt thereof.

13. The process according to claim 12, wherein the oxidizing comprises treating with chromium trioxide and sulfuric acid.

14. The process according to claim 12, further comprising preparing the compound of Formula III, or salt thereof, by a process comprising deprotecting a compound of Formula IV:

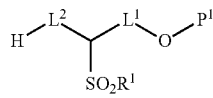

IV to form the compound of Formula III:

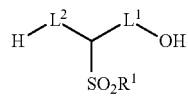

III wherein $P^1$ is a hydroxyl protecting group.

15. The process according to claim 14, wherein $P^1$ is tert-butyldimethylsilyl.

16. The process according to claim 14, wherein the deprotecting comprises treating with tetrabutylammonium fluoride.

17. The process according to claim 14, further comprising preparing the compound of Formula IV:

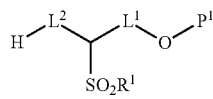

IV by a process comprising treating a compound of Formula V:

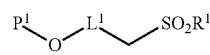

V with a strong base, followed by reacting with a compound of Formula VI:

VI to form the compound of Formula IV;
wherein Y is a leaving group.

18. The process according to claim 14, further comprising preparing the compound of Formula IV:

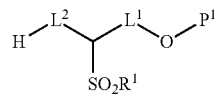

IV by a process comprising reacting a compound of Formula XII:

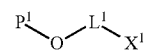

XII with a compound of Formula XIII:

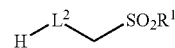

XIII to form the compound of Formula IV.

19. The process according to claim 17, wherein Y is p-toluenesulfonyloxy.

20. The process according to claim 17, wherein the strong base is n-butyllithium.

21. The process according to claim 17, further comprising preparing the compound of Formula V:

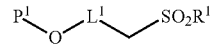

V by a process comprising oxidizing a compound of Formula VII:

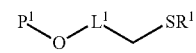

VII to form the compound of Formula V.

22. The process according to claim 21, wherein the oxidizing comprises treating with m-chloroperoxybenzoic acid.

23. The process according to claim 21, further comprising preparing the compound of Formula VII:

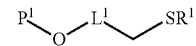

VII by a process comprising reacting a compound of Formula VIII:

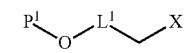

VIII with a compound of formula $R^1SH$ in the presence of a strong base to form the compound of Formula VII;
wherein X is a leaving group.

24. The process according to claim 23, wherein the strong base is sodium methoxide.

25. The process according to claim 23, wherein X is halogen.

26. The process according to claim 23, wherein X is bromo.

27. The process according to claim 23, further comprising preparing the compound of Formula VIII:

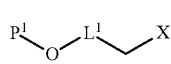
VIII by a process comprising protecting a compound of Formula IX:

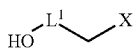
IX to form a compound of Formula VIII.

28. The process according to claim 17, further comprising preparing the compound of Formula VI:

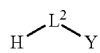
VI by a process comprising:
(a) reducing a compound of Formula X:

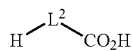
X or salt thereof, to form a compound of Formula XI:

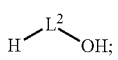
XI and
(b) converting the compound of Formula XI to the compound of Formula VI; wherein:
Y is a leaving group;
$L^2$ is selected from $C_{4-50}$ straight-chain alkylene and $C_{4-50}$ straight-chain alkenylene; each of which is optionally substituted with 1, 2, 3, 4, 5, or 6 independently selected $R^b$ groups; and
each $R^b$ is independently selected from $C_{1-30}$ alkyl and $C_{2-30}$ alkenyl.

29. A process according to claim 28, wherein the reducing comprises treating with lithium aluminum hydride.

30. A process according to claim 28, wherein Y is p-toluenesulfonyloxy.

31. A process according to claim 28, wherein the converting comprises reacting with p-toluenesulfonyl chloride.

* * * * *

UNITED STATES PATENT AND TRADEMARK OFFICE
CERTIFICATE OF CORRECTION

| | | |
|---|---|---|
| PATENT NO. | : 8,563,760 B2 | Page 1 of 1 |
| APPLICATION NO. | : 12/871043 | |
| DATED | : October 22, 2013 | |
| INVENTOR(S) | : Abdul H. Fauq and Albert O. Edwards | |

It is certified that error appears in the above-identified patent and that said Letters Patent is hereby corrected as shown below:

In the Claims

Column 71, line 47 (Claim 5), delete "di($C_{1-6}$ alkylamino," and insert -- di($C_{1-6}$ alkyl)amino, --, therefor.

Signed and Sealed this
First Day of July, 2014

Michelle K. Lee
*Deputy Director of the United States Patent and Trademark Office*